United States Patent
Tagge et al.

(10) Patent No.: US 7,037,990 B2
(45) Date of Patent: May 2, 2006

(54) TRANSITION METAL COMPLEXES IN THE CONTROLLED SYNTHESIS OF POLYOLEFINS SUBSTITUTED WITH FUNCTIONAL GROUPS

(75) Inventors: Christopher D. Tagge, San Carlos, CA (US); Robert B. Wilson, Jr., Palo Alto, CA (US); Hiroyuki Ono, Menlo Park, CA (US)

(73) Assignee: Nippon Synthetic Chemical Company, Osaka (JP)

( * ) Notice: Subject to any disclaimer, the term of this patent is extended or adjusted under 35 U.S.C. 154(b) by 0 days.

(21) Appl. No.: 10/336,666

(22) Filed: Jan. 3, 2003

(65) Prior Publication Data

US 2004/0132936 A1    Jul. 8, 2004

(51) Int. Cl.
- C08F 4/26 (2006.01)
- C08F 4/52 (2006.01)
- C08F 4/60 (2006.01)
- C08F 18/08 (2006.01)
- C08F 16/12 (2006.01)

(52) U.S. Cl. .......... 526/172; 526/161; 526/169.1; 526/166; 526/169; 526/131; 526/130; 526/134; 526/116; 526/115; 526/145; 526/332; 526/318; 526/318.5

(58) Field of Classification Search ............ 526/161, 526/160, 172, 170, 130, 332, 318, 318.5, 526/319, 320, 131, 145, 115, 116
See application file for complete search history.

(56) References Cited

U.S. PATENT DOCUMENTS

| | | | | |
|---|---|---|---|---|
| 5,866,663 | A | 2/1999 | Brookhart et al. | 526/170 |
| 5,880,241 | A | 3/1999 | Brookhart et al. | 526/343 |
| 6,066,603 | A * | 5/2000 | Emert et al. | 508/472 |
| 6,090,900 | A * | 7/2000 | Turner et al. | 526/269 |
| 6,107,422 | A * | 8/2000 | Wang et al. | 526/243 |
| 6,355,746 | B1 * | 3/2002 | Tagge et al. | 526/133 |
| 6,372,684 | B1 * | 4/2002 | Horton et al. | 502/155 |
| 6,436,864 | B1 * | 8/2002 | Tagge | 502/123 |
| 6,506,861 | B1 * | 1/2003 | Wang et al. | 526/172 |
| 6,593,440 | B1 * | 7/2003 | Sen et al. | 526/281 |
| 6,710,006 | B1 * | 3/2004 | De Boer et al. | 502/155 |
| 6,777,510 | B1 * | 8/2004 | Philipp et al. | 526/172 |
| 6,897,275 | B1 * | 5/2005 | Wang et al. | 526/161 |
| 2002/0032289 | A1 * | 3/2002 | Wang et al. | 526/171 |
| 2002/0099155 | A1 * | 7/2002 | Inoue et al. | 526/172 |

FOREIGN PATENT DOCUMENTS

| | | |
|---|---|---|
| EP | 1 134 236 A1 * | 3/2000 |
| WO | WO 96/23010 | 8/1996 |
| WO | WO 98/30612 | 7/1998 |
| WO | WO 98/49208 | 11/1998 |
| WO | WO 01/58874 A1 * | 8/2001 |

OTHER PUBLICATIONS

Albietz et al. Organometallics 1999, 18, 2747-2749.*
Johnson et al. (1996), "Copolymerization of Ethylene and Propylene with Functionalized Vinyl Monomers by Palladium(II) Catalysts," *J. Am. Chem. Soc.* 118(1):267-268.
Mecking et al. (1998), "Mechanistic Studies of the Palladium-Catalyzed Copolymerization of Ethylene and β-Olefins with Methyl Acrylate," *J. Am. Chem. Soc.* 120(5): 888-899.
Ramakrishnan et al. (1990), "Poly(5-hydroxyoctenylene) and Its Derivatives: Synthesis via Metathesis Polymerization of an Organoborane Monomer," *Macromolecules* 23 (21):4519-4524.

* cited by examiner

*Primary Examiner*—David W. Wu
*Assistant Examiner*—Rip A. Lee
(74) *Attorney, Agent, or Firm*—Reed I. P. Law Group

(57) ABSTRACT

A method is provided for the polymerization of olefins substituted with a functional group using a transition metal catalyst that, by virtue of one or more stabilizing groups incorporated within the catalyst structure, "fixes" the stereoconfiguration of each olefinic monomer relative to the transition metal complex during each successive reaction in the polymerization process. The invention substantially reduces the likelihood of olefin rearrangement at the active site of the catalyst during polymerization. In one particular embodiment, the functional group is a polar, electron-donating group and the stabilizing group is a Lewis acid substituent; examples of polymers that can be prepared with such a system include poly(vinyl acetate), poly(vinyl alcohol), and poly(vinyl ethers). Novel complexes and catalyst systems useful in the polymerization method are also provided.

35 Claims, 14 Drawing Sheets

US 7,037,990 B2

TRANSITION METAL COMPLEXES IN THE CONTROLLED SYNTHESIS OF POLYOLEFINS SUBSTITUTED WITH FUNCTIONAL GROUPS

TECHNICAL FIELD

This invention relates generally to the use of single-site organometallic complexes as catalysts in the polymerization of olefins. More particularly, the invention relates to the use of transition metal complexes in the polymerization of olefins that are substituted with one or more functional groups. The invention further relates to novel transition metal complexes and catalyst systems useful in the aforementioned method.

BACKGROUND OF THE INVENTION

Interest in making well-defined linear polymers substituted with functional groups has been spurred, in part, by the commercial utility of ethylene-vinyl alcohol (EVOH) and poly(vinyl alcohol) (PVOH). EVOH and PVOH exhibit excellent barrier properties toward gases and hydrocarbons and have found use in the food packaging, biomedical, and pharmaceutical industries. See Lagaron et al. (2001) *Polym. Testing* 20:569–577, and Ramakrishnan (1991) *Macromolecules* 24:3753–3759. The polymers also provide extraordinary chemical and abrasion resistance. However, synthesis of these polyalcohols has required a circuitous and expensive route. Vinyl alcohol monomer tautomerizes to acetaldehyde, which precludes its use as a monomer.

As a result, the most widely employed synthetic route to EVOH is the free radical polymerization of ethylene and vinyl acetate to produce poly(ethylene vinyl acetate) (EVAc), which can then be converted to EVOH by saponification. See Mecking et al. (1998) *J. Am. Chem. Soc.* 120:888–899; and Ramakrishnan (1990) *Macromolecules* 23:4519–4524. These EVOH copolymers contain a degree of branching, much like low-density polyethylene (LDPE), and have a random distribution of alcohol functionality along the polymer backbone (Ramakrishnan (1991); Valenti et al. (1998) *Macromolecules* 31:2764–2773). PVOH is prepared in a similar manner by hydrolysis of poly(vinyl acetate), and analogous problems have been encountered. An additional drawback of the conventional processes for preparing these polymers, or other polyolefins substituted with functional groups, is that radical polymerization technology provides little means of controlling molecular weight (MW), molecular weight distributions (MWD), block structures, and incorporation of comonomers, and therefore enables poor control over the polymer's mechanical properties as well.

The direct incorporation of polar functional groups along the backbone of linear polymers has been made possible via ring-opening metathesis polymerization ("ROMP") due to the development of functional group-tolerant late transition metal olefin metathesis catalysts. For example, Hillmyer et al. has reported the ROMP of alcohol-, ketone-, halogen-, and acetate-substituted cyclooctenes with a ruthenium olefin metathesis catalyst (Hillmyer et al. (1995) *Macromolecules* 28: 6311–6316). The asymmetry of the substituted cyclooctene, however, resulted in head-to-head (HH), head-to-tail (HT), and tail-to-tail (TT) coupling, yielding a polymer with regiorandom placement of the functional groups. A similar problem was encountered by Chung et al., who reported the ROMP of a borane-substituted cyclooctene with an early transition metal catalyst followed by oxidation to yield an alcohol functionalized linear polymer (Ramakrishnan et al. (1990), supra). A solution to this regiorandom distribution of functional groups was reported by Valenti et al., who used the acyclic diene metathesis (ADMET) polymerization of an alcohol-containing symmetric diene (Valenti et al., supra; Schellekens et al. (2000) *J. Mol. Sci. Rev. Macromol. Chem. Phys.* C40:167–192)) However, the molecular weights of these polymers were restricted to <3×10$^4$ g/mol by ADMET, and their rich hydrocarbon content has limited the barrier properties of the final EVOH copolymers (Lagaron et al., supra).

Single-site organometallic catalysts have been shown to provide exceptional control of MW, MWD, microstructure, and thus the mechanical properties of the polymers synthesized. Recently, a number of researchers have developed second-generation single-site catalysts using late metal complexes with specially substituted diimine ligands. See, e.g., Mecking et al. (1998), supra; Johnson et al. (1996) *J. Am. Chem. Soc.* 118:267–268; and International Patent Publication No. WO 96/23010. These catalysts have the important advantages of relatively low cost, ease of synthesis and support, and, in certain cases, tolerance of functional groups. These catalysts have been used to create a new class of very highly branched polyethylene, high-density polyethylene, atactic polypropylene, and a variety of polymers incorporating functional monomers. The catalysts do not, however, allow for polymerization of vinyl acetate and alkyl vinyl ethers such as butyl vinyl ether.

Accordingly, there is a need in the art for a method of synthesizing polymers using catalysts that are tolerant of functional groups and a process that enables precise control over molecular weight and molecular weight distribution. Ideally, such a method would also be useful in the synthesis of stereoregular polymers.

SUMMARY OF THE INVENTION

The invention is directed to the aforementioned need in the art, and provides a highly effective polymerization process in which a polyolefin is synthesized using a transition metal catalyst that is not only tolerant of functional groups on olefinic monomers but also "fixes" the stereoconfiguration of each functionalized olefinic monomer relative to the transition metal complex during each successive reaction in the polymerization process. In this manner, rearrangement of the olefin at the active site of the complex is prevented, in turn reducing the likelihood of catalyst poisoning or other problems associated with the occurrence of an unwanted reaction, i.e., a reaction resulting from rearrangement of the olefin while associated with the active site of the catalyst.

In a first embodiment, then, the invention provides a method for preparing a polyolefin substituted with pendent functional groups, by contacting, under polymerization conditions:

(a) a functionalized olefinic monomer composed of an olefin substituted on an olefinic carbon atom with a functional group, with (b) a catalytically effective amount of a transition metal complex that facilitates stepwise polymer synthesis by successive insertion reactions of olefinic monomers, the complex comprising (i) a transition metal atom that serves as the active site to which the functionalized olefinic monomer binds during each of the successive reactions, and (ii) a ligand substituted with a stabilizing group that forms a noncovalent bond with the functional group and thereby maintains the functionalized olefinic monomer in a single stereochemical configuration relative to the transition metal complex throughout each successive reaction, thereby preventing rearrangement of the functionalized olefin relative to the transition metal complex during each reaction.

The interaction between the stabilizing group on the catalyst and the functional group on the olefin may involve hydrogen bonding, ionic bonding, or some other type of noncovalent bonding. Hydrogen bonds are formed between Lewis base substituents, such as polar, electron-donating groups, and Lewis acid substituents, such as boronato or dialkylaluminum groups. Often, the olefinic functional group is a polar, electron-donating group (e.g., an alkoxy, alkyl ether, or ester group) and the stabilizing group on the catalyst is a Lewis acid substituent. The method may be carried out using any of a variety of transition metal complexes as catalysts, e.g., Brookhart-type catalysts, metallocene catalysts, and the like. Single-site catalysts are strongly preferred, insofar as they provide exceptional control over molecular weight, molecular weight distribution, and microstructure, and can give rise to a stereoregular polyolefinic product.

This methodology provides a significant advance in the art with respect to commercially viable syntheses of important polyolefins such as PVOH and EVOH. That is, when the functionalized olefinic monomer is vinyl acetate, and the stabilizing group on the catalyst is a Lewis acid substituent, the polyolefin is poly(vinyl acetate), which can be readily hydrolyzed to give PVOH using straightforward and well-known methodology. When ethylene is employed as an olefinic comonomer, the resulting polyolefin is poly(ethylene vinyl acetate), which, again, can be readily converted to EVOH via hydrolysis. As another example, when the functionalized olefinic monomer is a vinyl ether (e.g., an alkyl vinyl ether), and the stabilizing group is a Lewis acid substituent, the resulting polyolefin is a poly(vinyl ether).

In another embodiment, a novel transition metal complex is provided that is useful in carrying out the aforementioned method. The complex has the structure of formula (I)

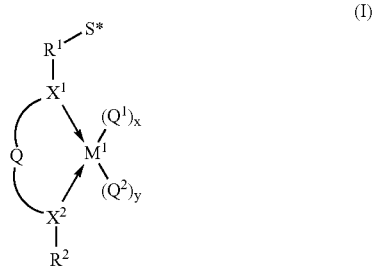

wherein:

$M^1$ is a transition metal having an oxidation state w;

x and y are integers in the range of zero to w, and the sum of x and y is w;

$X^1$ and $X^2$ are heteroatoms coordinated to $M^1$;

$R^1$ is hydrocarbylene, substituted hydrocarbylene, heteroatom-containing hydrocarbylene, or substituted heteroatom-containing hydrocarbylene;

S* is the stabilizing group;

$R^2$ is hydrocarbyl, substituted hydrocarbyl, heteroatom-containing hydrocarbyl, substituted heteroatom-containing hydrocarbyl, or —$R^1$—S*;

Q is a hydrocarbylene, substituted hydrocarbylene, heteroatom-containing hydrocarbylene, or substituted heteroatom-containing hydrocarbylene linker, and further wherein two or more substituents on adjacent atoms within Q may be linked to form a cyclic group; and $Q^1$ and $Q^2$ are univalent radicals.

Generally, $M^1$ is selected from Pd(II), Fe(II), Co(II), Ni(II), V(IV), Zr(IV), Hf(IV), Ti(IV), Ru(II), Rh(II), Os(II), Ir(II), and Pt(II). The complexes may be positively charged and thus associated with a negatively charged counterion. That is, a metal complex of formula (I) may carry a positive charge +a, where a is an integer in the range of 1 through 4, more typically 1 or 2, and is associated with a/b anions each bearing a negative charge −b. The metal complex may also be a zwitterion, i.e., a complex wherein one atom or region bears a positive charge with another atom or region bearing a negative charge.

In another embodiment of the invention, a catalyst system is provided comprised of (1) a transition metal complex having the structure of formula (I), (2) a catalyst activator, and optionally (3) an inert diluent. Typical catalyst activators herein include salts or acids of a weakly coordinating anion such as fluorohydrocarbylborate ions, trifluoromethanesulfonate, p-toluenesulfonate, $SbF_6^-$, and $PF_6^-$, all of which give rise to a cationic catalyst associated with one of the aforementioned anions as counterions. Other catalyst activators herein are alkylaluminum reagents such as dialkylaluminum halides, which give rise to a zwitterionic catalyst. Accordingly, it will be appreciated that the catalyst activator is normally used to convert the electronically neutral transition metal to a cation, such that the catalyst is in the form of a cationic or zwitterionic complex.

DETAILED DESCRIPTION OF THE INVENTION

Figure 1:
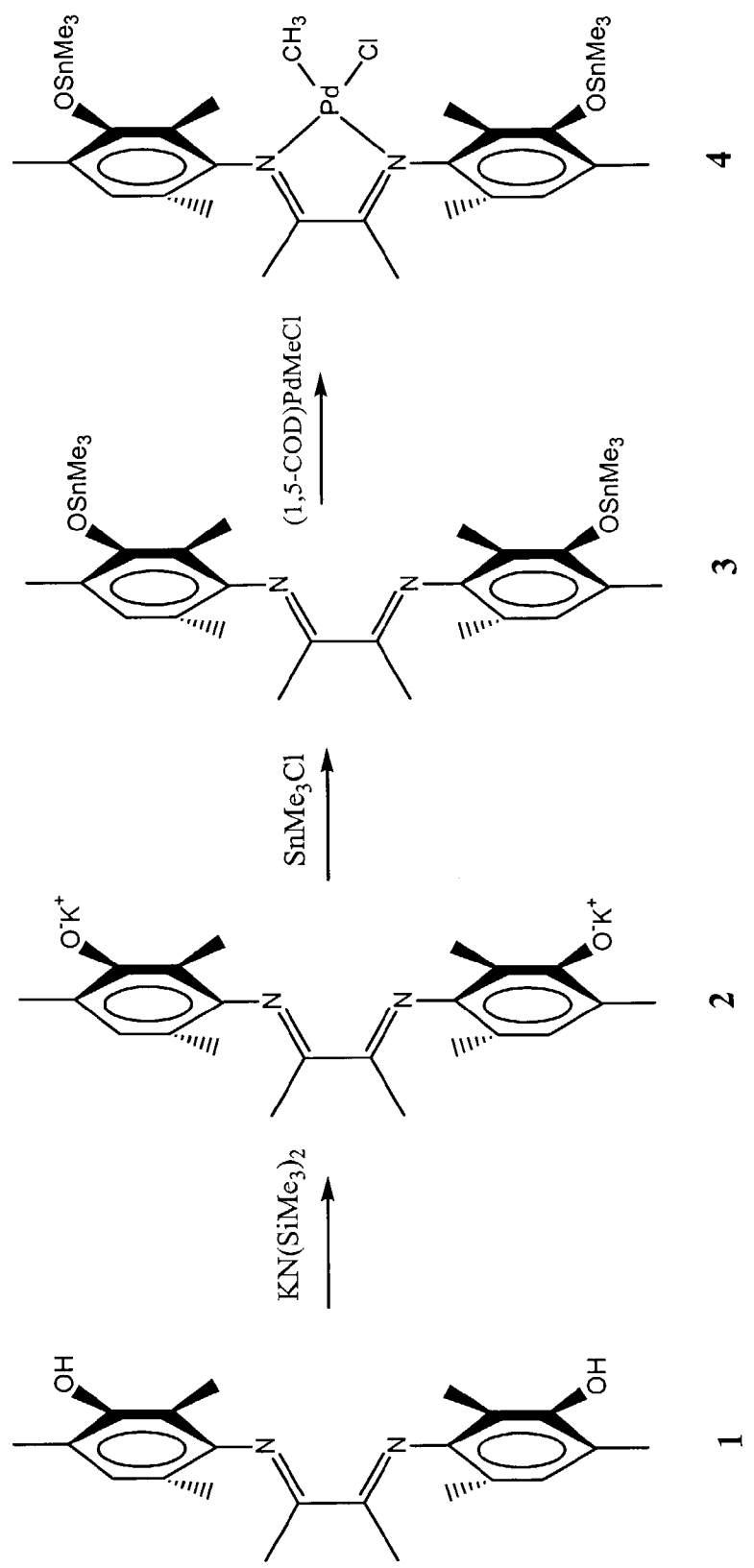
FIG. 1 schematically illustrates the synthesis of a representative Pd(II) catalyst of the invention, wherein an α-diimine ligand is substituted with —$OSn(CH_3)_3$ stabilizing groups, as described in Example 1.

Definitions and Nomenclature:

It is to be understood that unless otherwise indicated this invention is not limited to specific reactants, reaction conditions, ligands, transition metal complexes, or the like, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "a complex" encompasses a combination or mixture of different complexes as well as a single complex, reference to "a substituent" includes a single substituent as well as two or more substituent groups that may or may not be the same, and the like.

In this specification and in the claims that follow, reference will be made to a number of terms, which shall be defined to have the following meanings:

As used herein, the phrase "having the formula" or "having the structure" is not intended to be limiting and is used in the same way that the term "comprising" is commonly used.

The term "alkyl" as used herein refers to a linear, branched, or cyclic saturated hydrocarbon group typically although not necessarily containing 1 to about 20 carbon atoms, preferably 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The terms "alkylene" and "lower alkylene" as used herein refer to a difunctional linear, branched, or cyclic alkyl or lower alkyl group, respectively, where "alkyl" and "lower alkyl" are as defined above.

The term "alkenyl" as used herein refers to a linear, branched, or cyclic hydrocarbon group of 2 to about 20 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The terms "alkenylene" and "lower alkenylene" as used herein refer to a difunctional linear, branched, or cyclic alkenyl or lower alkenyl group, respectively, where "alkenyl" and "lower alkenyl" are as defined above.

The term "alkynyl" as used herein refers to a linear or branched hydrocarbon group of 2 to about 20 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The terms "alkynylene" and "lower alkynylene" as used herein refer to a difunctional linear, branched, or cyclic alkenyl or lower alkynyl group, respectively, where "alkynyl" and "lower alkynyl" are as defined above.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 20 carbon atoms and either one aromatic ring or 2 to 4 fused or linked aromatic rings, e.g., phenyl, naphthyl, biphenyl, and the like, with more preferred aryl groups containing 1 to 3 aromatic rings, and particularly preferred aryl groups containing 1 or 2 aromatic rings and 5 to 14 carbon atoms. "Substituted aryl" refers to an aryl moiety substituted with one or more substituent groups, and the terms "heteroatom-containing aryl" and "heteroaryl" refer to aryl in which at least one carbon atom is replaced with a heteroatom. Unless otherwise indicated, the terms "aromatic," "aryl," and "arylene" include heteroaromatic, substituted aromatic, and substituted heteroaromatic species.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 20 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Generally, alkaryl and aralkyl group contain 6 to 30 carbon atoms, preferably 6 to 24 carbon atoms, and particularly preferred alkaryl and aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The terms "alkarylene" and "aralkylene" are analogous to "alkaryl" and "aralkyl" as just defined, but are difunctional rather than monofunctional. That is, an "alkarylene" moiety refers to an arylene linkage substituted with an alkyl group, while an "aralkylene" moiety refers to an alkylene linkage substituted with an aryl group.

The terms "halo," "halide," and "halogen" are used in the conventional sense to refer to a chloro, bromo, fluoro, or iodo substituent. The terms "haloalkyl," "haloalkenyl," and "haloalkynyl" (or "halogenated alkyl," "halogenated alkenyl," and "halogenated alkynyl") refer to an alkyl, alkenyl, or alkynyl group, respectively, in which at least one of the hydrogen atoms in the group has been replaced with a halogen atom.

"Hydrocarbyl" refers to univalent hydrocarbyl radicals containing 1 to about 30 carbon atoms, preferably 1 to about 20 carbon atoms, more preferably 1 to about 12 carbon atoms, including linear, branched, cyclic, saturated, and unsaturated species, such as alkyl groups, alkenyl groups, aryl groups, and the like. The term "lower hydrocarbyl" intends a hydrocarbyl group of 1 to 6 carbon atoms, and the term "hydrocarbylene" intends a divalent hydrocarbyl moiety containing 1 to about 30 carbon atoms, preferably 1 to about 20 carbon atoms, most preferably 1 to about 12 carbon atoms, including linear, branched, cyclic, saturated, and unsaturated species. The term "lower hydrocarbylene" intends a hydrocarbylene group of 1 to 6 carbon atoms. Unless otherwise indicated, the terms "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage, or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc. It should be noted that a "heterocyclic" group or compound may or may not be aromatic, and further that "heterocycles" may be monocyclic, bicyclic, or polycyclic as described above with respect to the term "aryl."

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with a non-hydrogen substituent. Examples of such substituents include, without limitation: functional groups such as hydroxyl, $C_1$–$C_{20}$ alkoxy, $C_2$–$C_{20}$ alkenyloxy, $C_2$–$C_{20}$ alkynyloxy, $C_5$–$C_{20}$ aryloxy, $C_2$–$C_{20}$ alkylcarbonyl, $C_6$–$C_{20}$ arylcarbonyl, $C_2$–$C_{20}$ alkylcarbonyloxy, $C_6$–$C_{20}$ arylcarbonyloxy, $C_2$–$C_{20}$ alkoxycarbonyl, $C_6$–$C_{20}$ aryloxycarbonyl, carboxy, carboxylato, carbamoyl, mono-($C_1$–$C_{20}$ alkyl)-substituted carbamoyl, di-($C_1$–$C_{20}$ alkyl)-substituted carbamoyl, mono-($C_1$–$C_{20}$ alkyl)-substituted $C_6$–$C_{20}$ arylcarbamoyl, di-($C_1$–$C_{20}$ alkyl)-substituted $C_6$–$C_{20}$ arylcarbamoyl, mono-($C_1$–$C_{20}$ alkyl)-substituted amino, di-($C_1$–$C_{20}$ alkyl)-substituted amino, mono-($C_5$–$C_{20}$ aryl)-substituted amino, di-($C_5$–$C_{20}$ aryl)-substituted amino, $C_2$–$C_{20}$ alkylamido, $C_6$–$C_{20}$ arylamido, imino, alkylimino, and arylimino; and the hydrocarbyl moieties $C_1$–$C_{20}$ alkyl (preferably $C_1$–$C_{18}$ alkyl, more preferably $C_1$–$C_{12}$ alkyl, most preferably $C_1$–$C_6$ alkyl), $C_2$–$C_{20}$ alkenyl (preferably $C_2$–$C_{18}$ alkenyl, more preferably $C_2$–$C_{12}$ alkenyl, most preferably $C_2$–$C_6$ alkenyl), $C_2$–$C_{20}$ alkynyl (preferably $C_2$–$C_{18}$ alkynyl, more preferably $C_2$–$C_{12}$ alkynyl, most preferably $C_2$–$C_6$ alkynyl), $C_5$–$C_{20}$ aryl (preferably $C_5$–$C_{14}$ aryl), $C_6$–$C_{24}$ alkaryl (preferably $C_6$–$C_{18}$ alkaryl), and $C_6$–$C_{24}$ aralkyl (preferably $C_6$–$C_{18}$ aralkyl).

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. That is, the phrase "substituted alkyl, alkenyl, and alkynyl" is to be interpreted as "substituted alkyl, substituted alkenyl, and substituted alkynyl." Analogously, the term "optionally substituted alkyl, alkenyl, and alkynyl" is to be interpreted as "optionally substituted alkyl, optionally substituted alkenyl, and optionally substituted alkynyl," and a "bridged bicyclic or polycyclic olefin monomer" is to be interpreted as a "bridged bicyclic olefin monomer" or a "bridged polycyclic olefin monomer."

The term "stereoregular polymer" is used to refer to a polymer with a regular arrangement of the "connectivity" between the monomer units.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

In the molecular structures herein, the use of bold and dashed lines to denote particular conformation of groups follows the IUPAC convention. A bond indicated by a broken line indicates that the group in question is below the general plane of the molecule as drawn (the "α" configuration), and a bond indicated by a bold line indicates that the group at the position in question is above the general plane of the molecule as drawn (the "β" configuration).

Catalysts:

The catalysts of the invention are transition metal complexes composed of (i) a transition metal atom that serves as the active site to which a functionalized olefinic monomer binds during each step of an insertion polymerization reaction, and (ii) a ligand substituted with a stabilizing group that forms a noncovalent bond with the functional group during each of the aforementioned steps. The stabilizing group may be one that forms a hydrogen bond with a particular functional group, as is the case with a stabilizing group in the form of a Lewis acid substituent when the functional group is a Lewis base substituent (e.g., a polar, electron-donating group), or with a stabilizing group in the form of a Lewis base substituent when the functional group is a Lewis acid. As another example, the stabilizing group may be selected so as to form an ionic bond with the functional group of an olefinic monomer, in which case one of the stabilizing group and the functional group is cationic, while the other is anionic. Preferred transition metal complexes contain a single transition metal atom, such that the complex is a single site transition metal catalyst. Single site catalysts are quite advantageous insofar as they allow for precise control over the molecular weight, molecular weight distribution, and microstructure of the polyolefin prepared, and can give rise to a stereoregular polymer.

In one embodiment, the transition metal complex used as the catalyst has the structure of formula (I)

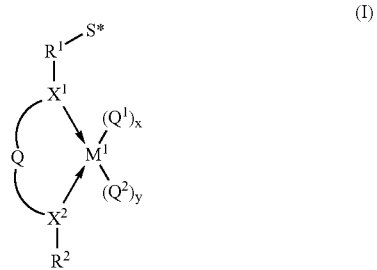

(I)

In structure (I), the various substituents are as follows.

$M^1$ is a transition metal having an oxidation state w, generally selected from Pd(II), Fe(II), Co(II), Ni(II), V(IV), Zr(IV), Hf(IV), Ti(IV), Ru(II), Rh(II), Os(II), Ir(II), and Pt(II), x and y are integers in the range of zero to w, and the sum of x and y is w when $M^1$ is in electronically neutral form. In a preferred embodiment, w is 2, $M^1$ is Pd(II), Fe(II), Co(II), or Ni(II), x is 1, and y is 1.

$X^1$ and $X^2$ are heteroatoms coordinated to $M^1$, and are preferably N or P, most preferably N.

$R^1$ is hydrocarbylene (e.g., $C_1$–$C_{20}$ alkylene, $C_2$–$C_{20}$ alkenylene, $C_2$–$C_{20}$ alkynylene, $C_5$–$C_{20}$ arylene, $C_6$–$C_{24}$ alkarylene, or $C_6$–$C_{24}$ aralkylene), substituted hydrocarbylene (e.g., substituted $C_1$–$C_{20}$ alkylene, $C_2$–$C_{20}$ alkenylene, $C_2$–$C_{20}$ alkynylene, $C_5$–$C_{20}$ arylene, $C_6$–$C_{24}$ alkarylene, or $C_6$–$C_{24}$ aralkylene), heteroatom-containing hydrocarbylene (e.g., $C_1$–$C_{20}$ heteroalkylene, $C_5$–$C_{20}$ heteroarylene, heteroatom-containing $C_6$–$C_{24}$ aralkylene, or heteroatom-containing $C_6$–$C_{24}$ alkarylene), or substituted heteroatom-containing hydrocarbylene (e.g., substituted $C_1$–$C_{20}$ heteroalkylene, $C_5$–$C_{20}$ heteroarytene, heteroatom-containing $C_6$–$C_{24}$ aralkylene,or heteroatom-containing $C_6$–$C_{24}$ alkarylene). $R^1$ may also be linked to an atom contained within the linkage Q. Preferred $R^1$ groups include, without limitation, $C_5$–$C_{14}$ arylene, substituted $C_5$–$C_{14}$ arylene, $C_5$–$C_{14}$ heteroarylene, and substituted $C_5$–$C_{14}$ heteroarylene, with more preferred $R^1$ groups selected from $C_5$–$C_{14}$ arylene and substituted $C_5$–$C_{14}$ arylene. Most preferred $R^1$ groups are phenylene and mono-, di-, and tri(lower alkyl)-substituted phenylene. When $R^1$ is bound to an atom within the linkage Q, it will be appreciated that the resulting cyclic group will be an N-heterocycle. Preferred cyclic groups in such a case are five-and six-membered rings, typically aromatic rings such as pyridine and substituted pyridine groups.

S* is the stabilizing group, and will in many cases be a Lewis acid substituent so as to provide stabilization of a polar, electron-donating group present on an olefinic monomer. Suitable Lewis acid substituents will be apparent to those of ordinary skill in the art, and include, by way of example, —$OBE_2$, —$OAlE_2$, —$OPE_2$, —$OSnE_3$, —$OSiE_3$, and —OZnE, wherein E is selected from halide, hydroxyl, $C_1$–$C_{12}$ alkyl, $C_1$–$C_{12}$ alkoxy, $C_5$–$C_{14}$ aryl, $C_5$–$C_{14}$ aryloxy, and the like, preferably halide, lower alkyl, and lower alkoxy. Of the aforementioned Lewis acid substituents, the more common substituents are —$OBE_2$, —$OAlE_2$, —$OSnE_3$, and —OZnE wherein E is chloro, bromo, alkoxy, or lower alkyl, or phenyl. Specific and preferred examples of Lewis acid substituents include, without limitation, —OBcat, where "cat" represents catechol,

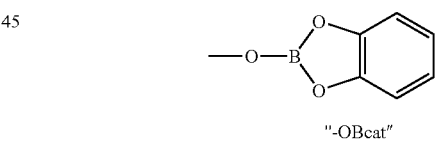

"-OBcat"

—$OAlCl_2$, —$OAl(CH_3)_2$, —$OSn(CH_3)_3$, and —OZnOPh (wherein Ph represents phenyl). In some cases, a hydrogen atom per se can act as a Lewis acid stabilizing group in the present context. Lewis acid substituents will noncovalently bind to polar, electron-donating groups such as hydroxyl, $C_1$–$C_{20}$ alkoxy, $C_2$–$C_{20}$ alkenyloxy, $C_2$–$C_{20}$ alkynyloxy, $C_5$–$C_{20}$ aryloxy, $C_2$–$C_{20}$ alkylcarbonyl, $C_6$–$C_{20}$ arylcarbonyl, $C_2$–$C_{20}$ alkylcarbonyloxy, $C_6$–$C_{20}$ arylcarbonyloxy, $C_2$–$C_{20}$ alkoxycarbonyl, $C_6$–$C_{20}$ aryloxycarbonyl, carboxy, carboxylato, carbamoyl, mono-($C_1$–$C_{20}$ alkyl)-substituted carbamoyl, di-($C_1$–$C_{20}$ alkyl)-substituted carbamoyl, mono-($C_1$–$C_{20}$ alkyl)-substituted $C_6$–$C_{20}$ arylcarbamoyl, di-($C_1$–$C_{20}$ alkyl)-substituted $C_6$–$C_{20}$ arylcarbamoyl, mono-($C_1$–$C_{20}$ alkyl)-substituted amino, di-($C_1$–$C_{20}$ alkyl)-substituted amino, mono-($C_5$–$C_{20}$ aryl)-substituted amino, di-($C_5$–$C_{20}$ aryl)-substituted amino, $C_2$–$C_{20}$ alkylamido, $C_6$–$C_{20}$ arylamido, imino, alkylimino, and arylimino substituents on the olefinic monomer undergoing polymerization.

$R^2$ is hydrocarbyl (e.g., $C_1$–$C_{20}$ alkyl, $C_2$–$C_{20}$ alkenyl, $C_2$–$C_{20}$ alkynyl, $C_5$–$C_{20}$ aryl, $C_6$–$C_{24}$ alkaryl, or $C_6$–$C_{24}$ aralkyl), substituted hydrocarbyl (e.g., substituted $C_1$–$C_{20}$ alkyl, $C_2$–$C_{20}$ alkenyl, $C_2$–$C_{20}$ alkynyl, $C_5$–$C_{20}$ aryl, $C_6$–$C_{24}$ alkaryl, or $C_6$–$C_{24}$ aralkyl), heteroatom-containing hydrocarbyl (e.g., $C_1$–$C_{20}$ heteroalkyl, $C_5$–$C_{20}$ heteroaryl, heteroatom-containing $C_6$–$C_{24}$ aralkyl, or heteroatom-containing $C_6$–$C_{24}$ alkaryl), or substituted heteroatom-containing hydrocarbyl (e.g., substituted $C_1$–$C_{20}$ heteroalkyl, $C_5$–$C_{20}$ heteroaryl, heteroatom-containing $C_6$–$C_{24}$ aralkyl, or heteroatom-containing $C_6$–$C_{24}$ alkaryl), and may also be substituted with a stabilizing group S* that may or may not be the same as the stabilizing group bound to $R^1$. $R^2$ may also be linked to an atom contained within the linkage Q. Preferred $R^2$ groups include, without limitation, $C_5$–$C_{14}$ aryl, substituted $C_5$–$C_{14}$ aryl, $C_5$–$C_{14}$ heteroaryl, and substituted $C_5$–$C_{14}$ heteroaryl, with more preferred $R^2$ groups selected from $C_5$–$C_{14}$ aryl and substituted $C_5$–$C_{14}$ aryl. When $R^2$ is bound to an atom within the linkage Q, it will be appreciated that the resulting cyclic group will be an N-heterocycle. Preferred cyclic groups in such a case are five-and six-membered rings, typically aromatic rings.

In a most preferred embodiment, $R^1$ is phenyl or lower alkyl-substituted phenyl, and $R^2$ is linked to an adjacent carbon atom contained within the linkage Q to form a pyridine ring.

Q is a hydrocarbylene (e.g., $C_1$–$C_{20}$ alkylene, $C_2$–$C_{20}$ alkenylene, $C_2$–$C_{20}$ alkynylene, $C_5$–$C_{20}$ arylene, $C_6$–$C_{24}$ alkarylene, or $C_6$–$C_{24}$ aralkylene), substituted hydrocarbylene (e.g., substituted $C_1$–$C_{20}$ alkylene, $C_2$–$C_{20}$ alkenylene, $C_2$–$C_{20}$ alkynylene, $C_5$–$C_{20}$ arylene, $C_6$–$C_{24}$ alkarylene, or $C_6 C_{24}$ aralkylene), heteroatom-containing hydrocarbylene (e.g., $C_1$–$C_{20}$ heteroalkylene, $C_5$–$C_{20}$ heteroarylene, heteroatom-containing $C_6$–$C_{24}$ aralkylene, or heteroatom-containing $C_6$–$C_{24}$ alkarylene), or substituted heteroatom-containing hydrocarbylene (e.g., substituted $C_1$–$C_{20}$ heteroalkylene, $C_5$–$C_{20}$ heteroarylene, heteroatom-containing $C_6$–$C_{24}$ aralkylene, or heteroatom-containing $C_6$–$C_{24}$ alkarylene) linker, and further wherein two or more substituents on adjacent atoms within Q may be linked to form a cyclic group, or wherein at least one atom within Q is linked to $R^1$ and/or $R^2$. Preferred Q linkages include, without limitation, $C_2$–$C_{12}$ alkenylene, substituted $C_2$–$C_{12}$ alkenylene, $C_2$–$C_{12}$ heteroalkenylene, and substituted $C_2$–$C_{12}$ heteroalkenylene, with more preferred Q linkages selected from $C_2$–$C_6$ alkenylene and substituted $C_2$–$C_6$ alkenylene.

$Q^1$ and $Q^2$ are each a univalent radical, and are preferably independently selected from hydrogen, halide, $C_1$–$C_{20}$ alkoxy, amido, and substituted or unsubstituted $C_1$–$C_{30}$ hydrocarbyl; if substituted, the substituents are typically although not necessarily electron-withdrawing groups such as halide, alkoxy, a Group 4 element, or the like. Alternatively, $Q^1$ and $Q^2$ may together form an alkylidene olefin (i.e., $=CR_2$ wherein R is hydrogen or hydrocarbyl, typically lower alkyl), acetylene, or a five- or six-membered cyclic hydrocarbyl group. Preferred $Q^1$ and $Q^2$ moieties are hydrogen, halide, $C_1$–$C_{12}$ alkyl, and $C_1$–$C_{12}$ alkyl substituted with one or more halogen and/or alkoxy groups, typically one to six such groups, and $C_1$–$C_{12}$ alkyl substituted with a Group 4 element. Particularly preferred $Q^1$ and $Q^2$ moieties are hydrogen, chloride, iodide, bromide, and methyl.

Certain complexes of formula (I) are in the form of a salt, i.e., are positively charged and associated with a negatively charged counterion. In the former case, the positive charge will reside on the metal, in which case the sum of x and y is less than w, and the complex is associated with a free anion, e.g., a weakly coordinating anion. Preferred anions are preferably sterically bulky, so that the negative charge borne by the ion is delocalized. Weakly coordinating bulky anions are known to those of ordinary skill in the art, and include, by way of example and not limitation, fluorohydrocarbylborate ions, trifluoromethanesulfonate, $BF_4^-$, $Ph_4B^-$ (Ph=phenyl), p-toluenesulfonate, $SbF_6^-$, and $PF_6^-$. Particularly preferred such anions are the fluorohydrocarbylborate ions, e.g., tetrakis[3,5-bis(trifluoromethyl)phenyl]borate ($BAF^-$), tetra(pentafluorophenyl)borate, $H^+(OCH_2CH_3)_2$[(bis-3,5-trifluoromethyl)phenyl]borate, and trityltetra(pentafluorophenyl)borate.

Other complexes of formula (I) are zwitterionic, generally with a positive charge residing on the metal center (again, meaning that the sum of x and y is less than w), with a negative charge residing elsewhere within the complex, typically on an atom within a pendent group on a ligand. Zwitterions may be formed by reaction of an electronically neutral complex bearing an ionizable acidic group, e.g., a hydroxyl, sulfhydryl, or carboxyl group, with a Lewis base such as a dialkylaluminum halide (e.g., dimethylaluminum chloride). The complexes may be used as polymerization catalysts in salt or zwitterionic form, although more typically the complexes are used in electronically neutral form and rendered ionic or zwitterionic by admixture with the appropriate reagent in situ. In one preferred embodiment, Q has the structure of formula (II)

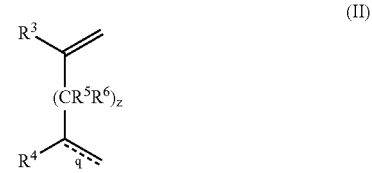

such that the transition metal complex has the structure of formula (III)

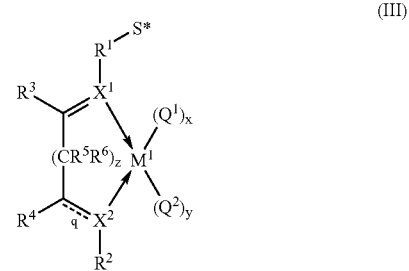

In formula (II) and formula (III): $R^1$, $R^2$, $M^1$, $X^1$, $X^2$, $Q^1$, $Q^2$, S*, x and y are as defined for complexes of formula (I); z is zero or 1; $R^3$ and $R^4$ are selected from hydrogen, hydrocarbyl (e.g., $C_1$–$C_{20}$ alkyl, $C_2$–$C_{20}$ alkenyl, $C_2$–$C_{20}$ alkynyl, $C_5$–$C_{20}$ aryl, $C_6$–$C_{24}$ alkaryl, or $C_6C_{24}$ aralkyl), substituted hydrocarbyl (e.g., substituted $C_1$–$C_{20}$ alkyl, $C_2$–$C_{20}$ alkenyl, $C_2$–$C_{20}$ alkynyl, $C_5$–$C_{20}$ aryl, $C_6$–$C_{24}$ alkaryl, or $C_6$–$C_{24}$ aralkyl), heteroatom-containing hydrocarbyl (e.g., $C_1$–$C_{20}$ heteroalkyl, $C_5$–$C_{20}$ heteroaryl, heteroatom-containing $C_6$–$C_{24}$ aralkyl, or heteroatom-containing $C_6$–$C_{24}$ alkaryl), and substituted heteroatom-containing hydrocarbyl (e.g., substituted $C_1$–$C_{20}$ heteroalkyl, $C_5$–$C_{20}$ heteroaryl, heteroatom-containing $C_6$–$C_{24}$ aralkyl, or heteroatom-containing $C_6$–$C_{24}$ alkaryl), and are preferably hydrogen or $C_1$–$C_{12}$ hydrocarbyl, more preferably hydrogen or lower alkyl, most preferably hydrogen or methyl; and $R^5$ and $R^6$ are selected from hydrogen, hydrocarbyl, substituted hydrocarbyl, heteroatom-containing hydrocarbyl, and heteroatom-containing substituted hydrocarbyl, as above, and are preferably hydrogen or lower alkyl, most preferably hydrogen.

In addition, any of $R^2$, $R^3$, $R^4$, $R^5$, and $R^6$ may be substituted with a Lewis acid stabilizing group S*, which may or may not be the same as the S* bound to $R^1$, and, furthermore, any two or more of $R^1$, $R^2$, $R^3$, $R^4$, $R^5$, and $R^6$ may be taken together to form a cyclic group. Optimally, (a) $R^1$ and $R^3$ and/or (b) $R^2$ and $R^4$ taken together form a cyclic group. When $R^1$ and $R^3$ and/or (b) $R^2$ and $R^4$ are linked, the cyclic structures so formed may be alicyclic or aromatic, including, for example, furanyl, pyrrolyl, thiophenyl, imidazolyl, pyrazolyl, oxathiolyl, pyridinyl, methylpyridinyl, ethylpyridinyl, pyridazinyl, pyrimidinyl, pyrazinyl, piperidinyl, piperazinyl, morpholinyl, tetrahydrothiophenyl, tetrahydrofuranyl, tetrahydropyranyl, 1,4-dioxanyl, etc. When $R^3$ and $R^4$ are linked, the resulting structures are alicyclic and may or may not contain heteroatoms; such moieties include, for example, cyclopentane, cyclohexane, tetrahydrofuran, tetrahydropyran, tetrahydrothiophene, 1,4-dioxane, 1,2-dithiole, 1,3-dithiole, piperazine, morpholine, and the like.

More preferred catalysts encompassed by formula (III) are those wherein z is zero, q is present as a double bond, x and y are 1, $X^1$ and $X^2$ are N, S* is a Lewis acid substituent, $R^1$ is phenylene or mono-, di-, or tri-(lower alkyl)-substituted phenylene, and $R^3$ is hydrogen or methyl, preferably methyl, and either (a) $R^2$ is phenyl or mono-, di-, or tri-(lower alkyl)-substituted phenyl and $R^4$ is identical to $R^3$, or (b) $R^2$ and $R^4$ together form a pyridine ring that may or may not be substituted with S* or other substituents, but is preferably unsubstituted, and $R^3$ is hydrogen. In addition, exemplary catalysts are wherein $M^1$ is Pd(II), Fe(II), Co(II), or Ni(II). Examples of these more preferred catalysts are represented by formulae (IV) and (V):

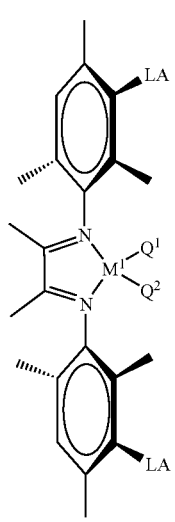

(IV)

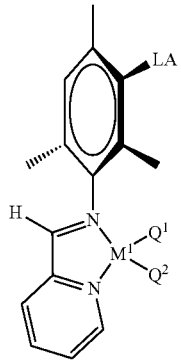

(V)

In structures (IV) and (V), $M^1$, $Q^1$, and $Q^2$ are as defined above, and LA is the Lewis acid substituent.

Complexes of formula (IV) are typically synthesized from the "DAD" (diazabuta-1,3-diene) precursor ligand Ar—N═C(Me)-C(Me)═N—Ar wherein Me is methyl, Ar is 2,4,6-trimethyl-3-Pr and Pr is the precursor to the Lewis acid substituent $L^A$. The Pr moiety is converted to the desired Lewis acid substituent by reaction with the appropriate reagent(s) to give the desired LA-substituted ligand, which may then be metallated. For example, a hydroxyl moiety can serve as Pr, in which case the ligand precursor can be converted to the desired ligand by deprotonation with a deprotonating reagent (such as potassium hexamethyldisilazide) to give the corresponding phenoxide, followed by reaction with $ME_C$-Lg to give the Lewis acid substituent -LA, which, in this case, will be the substituent —$OME_C$. M is normally B, Al, P, Sn, Si, or Zn, preferably B, Al, or Sn, E is as defined earlier, c is 1, 2, or 3, depending on M, and Lg is a leaving group such as a halide, particularly chloride. Representative such syntheses are described in Examples 1 and 6 herein.

Alternatively, the precursor ligand (again, Ar—N═C(Me)-C(Me)═N—Ar wherein Ar is 2,4,6-trimethyl-3-Pr and Pr is the precursor to the Lewis acid substituent LA) may be metallated and then converted in situ to the LA-substituted form of the catalyst by incorporation of a suitable catalyst activator into the reaction mixture, i.e., a salt or acid of a weakly coordinating anion and/or a reagent $ME_C$-Lg as described above. The catalyst activator also converts the metal site of the complex, if in electronically neutral form, to a cation, such that the complex is then cationic or zwitterionic. See Examples 2, 3, 4, and 10–15.

Complexes of formula (V) are synthesized in a similar manner from the "pyim" (pyridyl imine) precursor ligand Ar—N═C(H)-2-pyridine (Ar=2,4,6-trimethyl-3-hydroxyphenyl), as described in Examples 5, 7, 8, and 9.

Catalysts in the form of salts and zwitterions corresponding to complexes of formula (IV) are shown below as structures (IVA) and (IVB), respectively,

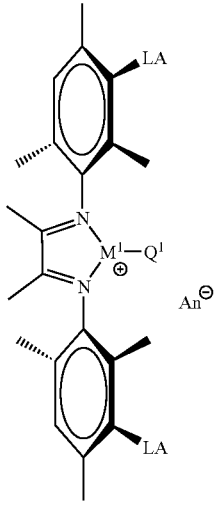

(IVA)

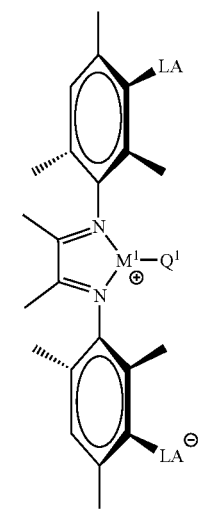

(IVB)

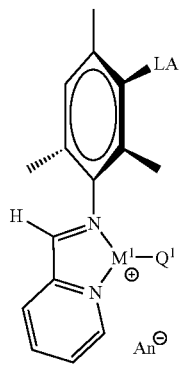

(VA)

where An⁻ is a negatively charged counterion (e.g., a weakly coordinating anion as described elsewhere herein), while catalysts in the form of salts and zwitterions corresponding to complexes of formula (V) are shown below as structures (VA) and (VB), respectively.

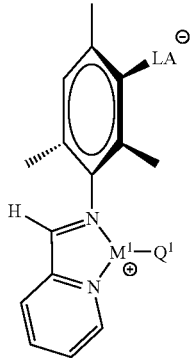

(VB)

In another embodiment, the transition metal complex used as the olefin polymerization catalyst herein is that described in U.S. Pat. No. 6,355,746 to Tagge et al., assigned to SRI International (Menlo Park, Calif.). In one embodiment, the complex is of the formula $L^1[M^2Q^1Q^2]L^2$ wherein $M^2$ is a mid-transition metal, $Q^1$ and $Q^2$ are univalent radicals as defined above, and $L^1$ and $L^2$ are nitrogenous ligands, at least one of which is substituted with the stabilizing group S* as described above. Each of $L^1$ and $L^2$ contains a nitrogen atom within a C=N group and a second coordinating atom that is either a second nitrogen atom, optionally present in a second C=N group, or an oxygen, sulfur, or phosphorus atom.

In a related embodiment, as also described in U.S. Pat. No. 6,355,746 to Tagge et al., the catalyst is a transition metal complex having the structure of formula (VI)

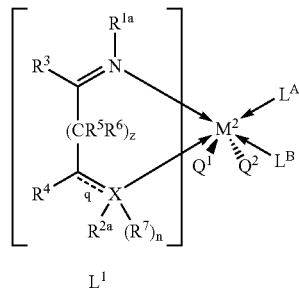

(VI)

wherein:

$M^2$ is a mid-transition metal typically selected from Mb, Ta, Mo, W, Mn, and Re, and $Q^1$, $Q^2$, $R^3$, $R^4$, $R^5$, $R^6$, q, and z are as defined above;

n is zero or 1;

$R^{1a}$, $R^{2a}$, and $R^7$ are defined as for $R^2$, and further wherein any two or more of $R^{1a}$, $R^{2a}$, $R^3$, $R^4$, $R^5$, $R^6$, and $R^7$ may together form a cyclic group as described for complexes of formula (III);

$L^A$ and $L^B$ are ligands that may be the same or different and are selected from the group consisting of nitrogen-containing, sulfur-containing and oxygen-containing heterocycles, tertiary amines and phosphines, or $L^A$ and $L^B$ may together form a single bidentate ligand $L^2$ as above, which may or may not be the same as $L^1$; and wherein at least one of $R^{1a}$, $R^{2a}$, $R^5$, $R^6$, and $R^7$, preferably at least one of $R^{1a}$, $R^{2a}$, and/or $R^7$, is substituted with the stabilizing group S*.

$L^A$ and $L^B$ are generally selected from: nitrogen-containing heterocycles such as pyridine, pyridazine, pyrimidine, pyrazine, 1,3,5-triazine, 1,2,4-triazine, 1,2,3-triazine, pyrrole, 2H-pyrrole, 3H-pyrrole, pyrazole, 2H-imidazole, 1,2,3-triazole, 1,2,4-triazole, indole, 3H-indole, 1H-isoindole, cyclopenta(b)pyridine, indazole, quinoline, isoquinoline, cinnoline, quinazoline, naphthyridine, piperidine, piperazine, pyrrolidine, pyrazolidine, quinuclidine, and imidazolidine; sulfur-containing heterocycles such as thiophene, 1,2-dithiole, 1,3-dithiole, thiepin, benzo(b)thiophene, and benzo(c)thiophene; oxygen-containing heterocycles such as 2H-pyran, 4H-pyran, 2-pyrone, 4-pyrone, 1,2-dioxin, 1,3-dioxin, oxepin, furan, 2H-1-benzopyran, coumarin, chroman-4-one, isochromen-1-one, isochromen-3-one, xanthene, tetrahydrofuran, and 1,4-dioxan; mixed heterocycles such as isoxazole, oxazole, thiazole, isothiazole, 1,2,3-oxadiazole, 1,2,4-oxadiazole, 1,3,4-oxadiazole, 1,2,3,4-oxatriazole, 1,2,3,5-oxatriazole, 3H-1,2,3-dioxazole, 3H-1,2-oxathiole, 1,3-oxathiole, 4H-1,2-oxazine, 2H-1,3-oxazine, 1,4-oxazine, 1,2,5-oxathiazine, o-isooxazine, pyrano[3,4-b]pyrrole, indoxazine, benzoxazole, anthranil, and morpholine; tertiary amines, particularly trialkylamines, and preferably tri(lower alkyl)amines such as triethylamine, methyldiethylamine, trimethylamine, methyldiisopropylamine, and the like; phosphines, particularly trialkylphosphines, and preferably tri(lower alkyl)phosphines such as triethylphosphine, methyldiethylphosphine, trimethylphosphine, methyldiisopropylphosphine, and the like. In a particularly preferred embodiment, however, $L^A$ and $L^B$ may also be taken together to form a single bidentate ligand $L^2$ wherein $L^2$ is as defined above and, optimally, is identical to $L^1$.

As also described in U.S. Pat. No. 6,355,746 to Tagge et al., an exemplary such compound has the structure of formula (VII)

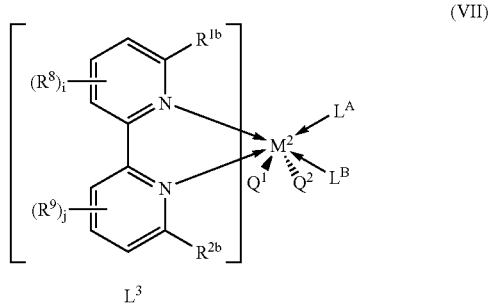

(VII)

wherein:

i and j are independently zero, 1, 2, or 3; and $R^{1b}$ and $R^{2b}$ are independently hydrogen or $C_1$–$C_{10}$ hydrocarbyl, $R^8$ and $R^9$ are independently $C_1$–$C_{10}$ hydrocarbyl or substituted $C_1$–$C_{10}$ hydrocarbyl, wherein at least one of $R^{1b}$, $R^{2b}$, $R^8$, and $R^9$ is substituted with the stabilizing group S*. Any two or more ortho $R^8$ moieties or $R^9$ moieties, when i or j, respectively, is greater than 2, may be taken together to form a further ring or rings, for example, a benzene ring.

In a related embodiment, the transition metal complex has the structure of formula (VIII)

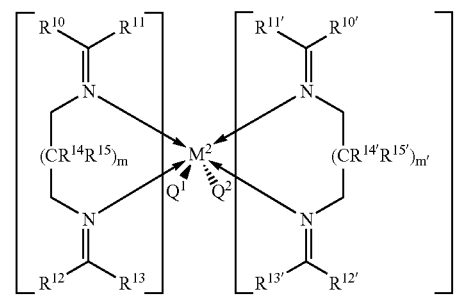

(VIII)

wherein:

$M^2$, $Q^1$, and $Q^2$ are as defined previously;

$R^{10}$ is hydrocarbyl (e.g., $C_1$–$C_{20}$ alkyl, $C_2$–$C_{20}$ alkenyl, $C_2$–$C_{20}$ alkynyl, $C_5$–$C_{20}$ aryl, $C_6$–$C_{24}$ alkaryl, or $C_6$–$C_{24}$ aralkyl), substituted hydrocarbyl (e.g., substituted $C_1$–$C_{20}$ alkyl, $C_2$–$C_{20}$ alkenyl, $C_2$–$C_{20}$ alkynyl, $C_5$–$C_{20}$ aryl, $C_6$–$C_{24}$ alkaryl, or $C_6$–$C_{24}$ aralkyl), heteroatom-containing hydrocarbyl (e.g., $C_1$–$C_{20}$ heteroalkyl, $C_5$–$C_{20}$heteroaryl, heteroatom-containing $C_6$–$C_{24}$ aralkyl, or heteroatom-containing $C_6$–$C_{24}$ alkaryl), or substituted heteroatom-containing hydrocarbyl (e.g., substituted $C_1$–$C_{20}$ heteroalkyl, $C_5$–$C_{20}$ heteroaryl, heteroatom-containing $C_6$–$C_{24}$ aralkyl, or heteroatom-containing $C_6$–$C_{24}$ alkaryl), or $R^{10}$ and $R^{11}$ taken together form a ring;

$(R^{10})'$ is defined as for $R^{10}$ and $(R^{11})'$ is defined as for $R^{11}$, or $(R^{10})'$ and $(R^{11})'$ taken together form a ring;

$R^{12}$ is defined as for $R^{10}$ and $R^{13}$ is as defined for $R^{11}$, or $R^{12}$ and $R^{13}$ taken together form a ring;

$(R^{12})'$ is defined as for $R^{12}$ and $(R^{13})'$ is defined as for $R^{13}$, or $(R^{12})'$ and $(R^{13})'$ taken together form a ring;

$R^{14}$, $(R^{14})'$, $R^{15}$, and $(R^{15})'$ are independently selected from hydrogen, hydrocarbyl, substituted hydrocarbyl, heteroatom-containing hydrocarbyl, and substituted heteroatom-containing hydrocarbyl, as above, and are preferably hydrogen or lower alkyl, most preferably hydrogen; and m and m' are independently zero or 1, wherein at least one of $R^{10}$, $(R^{10})'$, $R^{11}$, $(R^{11})'$, $R^{12}$, $(R^{12})'$, $R^{13}$, $(R^{13})'$ $R^{14}$, $(R^{14})'$, $R^{15}$, and $(R^{15})'$, preferably at least one of $R^{10}$, $(R^{10})'$, $R^{11}$, $(R^{11})'$, $R^{12}$, $(R^{12})'$, $R^{13}$, and $(R^{13})'$, is substituted with the stabilizing group S* as defined previously.

Complexes of formulae (VI), (VII), and (VIII) may be synthesized using the methodology described in U.S. Pat. No. 6,355,746. Generally, ligands of the diimine type (i.e., "DAD" ligands) are synthesized from a 1,2-diketone by addition of a primary amine. See, e.g., U.S. Pat. Nos. 5,866,663, 5,880,241, and 6,355,746, and International Patent Publication Nos. WO 98/30612 and WO 98/49208. Other ligands containing one or more C=N groups may be synthesized in a similar manner, by reaction of a suitable primary amine with a selected aldehyde or a ketone. For example, the asymmetric ligand

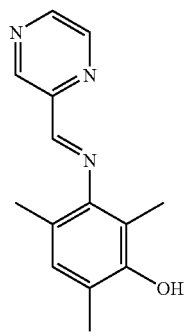

may be readily synthesized from 3-amino-2,4,6-trimethylphenol and pyridine carboxaldehyde, as described in Example 5. Weidenbruch et al. (1993) *Organometallic Chemistry* 454:35 and Patai, Ed., *The Chemistry of the Carbon-Nitrogen Double Bond* (New York: John Wiley & Sons, February 1970), which provides information on various synthetic methods that can be used in the preparation of imines.

In complex (VI), $L^A$ and $L^B$ may be taken together to form a linkage having the formula -Cp(R)$_i$—B-T-, resulting in a cyclic group containing $M^2$, such that the transition metal complex has the structure of formula (IX)

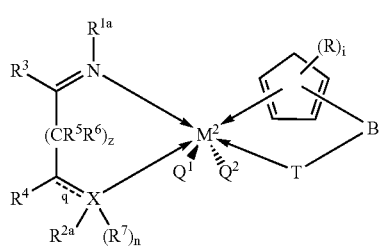

(IX)

wherein $M^2$, $Q^1$, $Q^2$, $R^{1a}$, $R^{2a}$, $R^3$, $R^4$, $R^5$, $R^6$, $R^7$, n, q, and z are defined as for complexes of formula (VI), again with the proviso that at least one of $R^{1a}$, $R^{2a}$, and $R^7$ is substituted with the stabilizing group S*, and further wherein any two or more of $R^{1a}$, $R^{2a}$, $R^3$, $R^4$, $R^5$, $R^6$, and $R^7$ may together form a cyclic group as described previously, i is zero, 1, 2, 3, or 4, and R, T, and B are as follows:

R is halide, hydrocarbyl (e.g., $C_1$–$C_{20}$ alkyl, $C_2$–$C_{20}$ alkenyl, $C_2$–$C_{20}$ alkynyl, $C_5$–$C_{20}$ aryl, $C_6$–$C_{24}$ alkaryl, or $C_6$–$C_{24}$ aralkyl), substituted hydrocarbyl (e.g., substituted $C_1$–$C_{20}$ alkyl, $C_2$–$C_{20}$ alkenyl, $C_2$–$C_{20}$ alkynyl, $C_5$–$C_{20}$ aryl, $C_6$–$C_{24}$ alkaryl, or $C_6$–$C_{24}$ aralkyl), heteroatom-containing hydrocarbyl (e.g., $C_1$–$C_{20}$ heteroalkyl, $C_5$–$C_{20}$ heteroaryl, heteroatom-containing $C_6$–$C_{24}$ aralkyl, or heteroatom-containing $C_6$–$C_{24}$ alkaryl), or substituted heteroatom-containing hydrocarbyl (e.g., substituted $C_1$–$C_{20}$ heteroalkyl, $C_5$–$C_{20}$ heteroaryl, heteroatom-containing $C_6$–$C_{24}$ aralkyl, or heteroatom-containing $C_6$–$C_{24}$ alkaryl), or, when i is 2 and two R groups are ortho with respect to each other, the two R groups can be linked to form an additional cyclic moiety. In preferred complexes, when i is nonzero, the R moiety or moieties are halide or $C_1$–$C_{12}$ alkyl, or two R substituents that are ortho to each other on the cyclopentadienyl ring may be taken together to form a five- or six-membered cyclic structure. This cyclic structure may be unsubstituted or substituted, preferably with halide or a hydrocarbyl group as explained above. Particularly preferred R groups are halide and lower alkyl; complexes wherein two R substituents are ortho to each other and linked to form an cyclopentadienyl ring (and therefore an indenyl moiety), optionally substituted with a lower alkyl group, are also particularly preferred.

T is cyclopentadienyl, indenyl, fluorenyl, indolyl, or aminoboratobenzyl, unsubstituted or substituted with R groups where R is as defined above, or T may be $J(R^T)_r$ where J is nitrogen, phosphorus, oxygen, or sulfur, the $R^T$ are each hydrogen, hydrocarbyl, halide-substituted hydrocarbyl, heteroatom-containing hydrocarbyl, or alkoxy, and r is the coordination number of J minus 2. Preferred T substituents are those having the formula $J(R^T)_r$ wherein J is nitrogen or phosphorus, r is 1, and $R^T$ is $C_1$–$C_{12}$ alkyl optionally substituted with one or more, typically one to six, halogen atoms. Particularly preferred T groups are $NR^T$ moieties wherein $R^T$ is lower alkyl or phenyl.

B is a nonmetallic linking moiety, e.g., hydrocarbylene (e.g., $C_1$–$C_{20}$ alkylene, $C_2$–$C_{20}$ alkenylene, $C_2$–$C_{20}$ alkynylene, $C_5$–$C_{20}$ arylene, $C_6$–$C_{24}$ alkarylene, or $C_6$–$C_{24}$ aralkylene), substituted hydrocarbylene (e.g., substituted $C_1$–$C_{20}$ alkylene, $C_2$–$C_{20}$ alkenylene, $C_2$–$C_{20}$ alkynylene, $C_5$–$C_{20}$ arylene, $C_6$–$C_{24}$ alkarylene, or $C_6$–$C_{24}$ aralkylene), heteroatom-containing hydrocarbylene (e.g., $C_1$–$C_{20}$ heteroalkylene, $C_5$–$C_{20}$ heteroarylene, heteroatom-containing $C_6$–$C_{24}$ aralkylene, or heteroatom-containing $C_6$–$C_{24}$ alkarylene), or substituted heteroatom-containing hydrocarbylene (e.g., substituted $C_1$–$C_{20}$ heteroalkylene, $C_5$–$C_{20}$ heteroarylene, heteroatom-containing $C_6$–$C_{24}$ aralkylene, or heteroatom-containing $C_6$–$C_{24}$ alkarylene). Preferred B linkages are substituted or unsubstituted $C_1$–$C_{12}$ alkylene and $C_5$–$C_{14}$ arylene.

In another embodiment, the transition metal complex has the structure of formula (VIII)

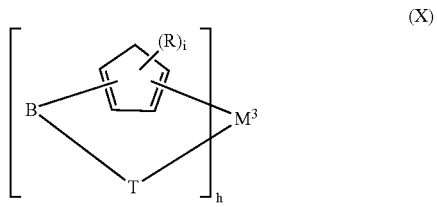

(X)

wherein:

h is 1 or 2;

i is zero, 1, 2, or 3;

$M^3$ is a Group 3 element, a Group 4 element, a Group 5 element, a lanthanide, or an actinide, and is substituted with two monovalent ligands or a divalent ligand when i is 1; and R, T, and B are as defined for complexes of formula (IX), wherein at least one of an R substituent and T is substituted with a stabilizing group S* as defined previously.

In still another embodiment, the transition metal complex has the structure of formula (XI)

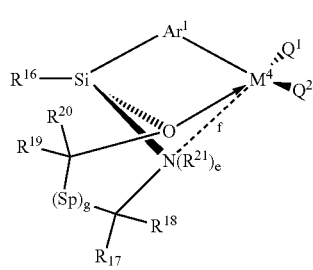

(XI)

wherein:

Ar$^1$ is an aromatic moiety containing 1 to 3 aromatic rings with at least one of the aromatic rings comprising a cyclopentadienyl group, wherein Ar$^1$ is optionally substituted with an $C_1$–$C_2$ alkyl or $C_5$–$C_{14}$ aryl substituent, and further wherein if Ar$^1$ contains 2 or 3 aromatic rings, the rings are preferably fused;

M$^4$ is a Group 3, Group 4, Group 5, Group 6, lanthanide or actinide metal;

Q$^1$ and Q$^2$ are as defined previously, and are preferably independently selected from halide, lower alkoxy, lower alkyl and amido;

R$^{16}$ is hydrocarbyl (e.g., $C_1$–$C_{20}$ alkyl, $C_2$–$C_{20}$ alkenyl, $C_2$–$C_{20}$ alkynyl, $C_5$–$C_{20}$ aryl, $C_6$–$C_{24}$ alkaryl, or $C_6$–$C_{24}$ aralkyl), substituted hydrocarbyl (e.g., substituted $C_1$–$C_{20}$ alkyl, $C_2$–$C_{20}$ alkenyl, $C_2$–$C_{20}$ alkynyl, $C_5$–$C_{20}$ aryl, $C_6$–$C_{24}$ alkaryl, or $C_6$–$C_{24}$ aralkyl), heteroatom-containing hydrocarbyl (e.g., $C_1$–$C_{20}$ heteroalkyl, $C_5$–$C_{20}$ heteroaryl, heteroatom-containing $C_6$–$C_{24}$ aralkyl, or heteroatom-containing $C_6$–$C_{24}$ alkaryl), or substituted heteroatom-containing hydrocarbyl (e.g., substituted $C_1$–$C_{20}$ heteroalkyl, $C_5$–$C_{20}$ heteroaryl, heteroatom-containing $C_6$–$C_{24}$ aralkyl, or heteroatom-containing $C_6$–$C_{24}$ alkaryl), preferably $C_1$–$C_{12}$ hydrocarbyl;

R$^{17}$, R$^{18}$, R$^{19}$, and R$^{20}$ are independently selected from hydrogen, $C_1$–$C_{12}$ alkyl, and $C_5$–$C_{14}$ aryl, and are preferably selected from hydrogen, lower alkyl, phenyl, and benzyl, and wherein R$^{19}$ and R$^{20}$ may be taken together to form a carbonyl group;

R$^{21}$ is hydrogen, hydrocarbyl, or substituted hydrocarbyl;

e is 0 or 1, f is a coordination bond when e is 1, and f is a covalent bond when e is 0, with the proviso that when R$^{21}$ is hydrogen, e is 0 and f is a covalent bond;

Sp is selected from —CR$^{22}_2$—, —CR$^{22}_2$—CR$^{22}_2$—, —O—, —S—, —NR$^{22}$—, —BR$^{22}$—, —C(O)— and combinations thereof, wherein R$^{22}$ is hydrogen, lower alkyl or $C_5$–$C_{14}$ aryl, with the proviso that Sp does not introduce more than 2 atoms between the adjacent carbon atoms; and g is 0 or 1, wherein at least one of R$^{17}$, R$^{18}$, R$^{19}$, R$^{20}$, and R$^{21}$, preferably at least R$^{21}$, is substituted with the stabilizing group S*.

In preferred such complexes: Ar$^1$ is cyclopentadienyl, cyclopentadienyl substituted with one, two, three or four lower alkyl substituents, indenyl, fluorenyl and indolyl; M$^4$ is a Group 4 metal; R$^{16}$ is $C_1$–$C_{12}$ alkyl or $C_2$–$C_{12}$ alkenyl; and g is 0.

In particularly preferred such complexes: Ar$^1$ is cyclopentadienyl, tetramethylcyclopentadienyl, indenyl, or fluorenyl; M$^4$ is selected from Ti, Zr, and Hf; and R$^{16}$ is lower alkyl or lower alkenyl.

Synthesis of catalysts having the structure of formula (XI) may be carried out using the methodology described in U.S. Pat. Nos. 6,048,992 and 6,369,253 to Wilson Jr. et al., both of which are assigned to SRI International (Menlo Park, Calif.).

The Olefinic Monomers:

The transition metal complexes described in the preceding section are useful as catalysts in the polymerization of olefins via an insertion polymerization reaction involving functionalized olefinic monomers and, optionally, olefinic co-monomers that may or may not be functionalized. The functionalized olefinic monomer has the structure R$^{23}$R$^{24}$C=CR$^{25}$(-[Ln]$_s$-Fn) wherein R$^{23}$, R$^{24}$, and R$^{25}$ are hydrogen or hydrocarbyl, preferably hydrogen or lower hydrocarbyl. Preferably, R$^{23}$ and R$^{24}$ are hydrogen and R$^{25}$ is lower alkyl, and, most preferably R$^{23}$, R$^{24}$, and R$^{25}$ are all hydrogen. Fn is a functional group as described below, Ln is one-atom to six-atom linkage, preferably $C_1$–$C_4$ hydrocarbyl or $C_1$–$C_4$ heteroatom-containing hydrocarbyl, and s is zero or 1, such that the linkage is optional.

The functional group Fn may be, for example, hydroxyl, $C_1$–$C_{20}$ alkoxy, $C_2$–$C_{20}$ alkenyloxy, $C_2$–$C_{20}$ alkynyloxy, $C_5$–$C_{20}$ aryloxy, $C_2$–$C_{20}$ alkylcarbonyl, $C_6$–$C_{20}$ arylcarbonyl, $C_2$–$C_{20}$ alkylcarbonyloxy, $C_6$–$C_{20}$ arylcarbonyloxy, $C_2$–$C_{20}$ alkoxycarbonyl, $C_6$–$C_{20}$ aryloxycarbonyl, carboxy, carboxylato, carbamoyl, mono-($C_1$–$C_{20}$ alkyl)-substituted carbamoyl, di-($C_1$–$C_{20}$ alkyl)-substituted carbamoyl, mono-($C_1$–$C_{20}$ alkyl)-substituted $C_6$–$C_{20}$ arylcarbamoyl, di-($C_1$–$C_{20}$ alkyl)-substituted $C_6$–$C_{20}$ arylcarbamoyl, mono-($C_1$–$C_{20}$ alkyl)-substituted amino, di-($C_1$–$C_{20}$ alkyl)-substituted amino, mono-($C_5$–$C_{20}$ aryl)-substituted amino, di-($C_5$–$C_{20}$ aryl)-substituted amino, $C_2$–$C_{20}$ alkylamido, $C_6$–$C_{20}$ arylamido, imino, alkylimino, or arylimino. Preferred functional groups include $C_1$–$C_{20}$ alkoxy, $C_2$–$C_{20}$ alkenyloxy, $C_2$–$C_{20}$ alkynyloxy, $C_5$–$C_{20}$ aryloxy, $C_2$–$C_{20}$ alkylcarbonyl, $C_6$–$C_{20}$ arylcarbonyl, $C_2$–$C_{20}$ alkylcarbonyloxy, $C_6$–$C_{20}$ arylcarbonyloxy, $C_2$–$C_{20}$ alkoxycarbonyl, and $C_6$–$C_{20}$ aryloxycarbonyl. Exemplary functionalized olefinic monomers include vinyl acetate and lower alkyl vinyl ethers (e.g., butyl vinyl ether).

The functionalized olefinic monomer may also be cyclic, in which case the functional group is bound to the monomer either (a) through a linking moiety Ln to an olefinic carbon atom, or (b) directly or through a linking moiety Ln to a nonolefinic carbon atom contained within the cyclic structure.

Olefinic co-monomers that may be copolymerized with the functionalized olefin include linear or branched olefins such as ethylene, propylene, 1-butene, 3-methyl-1-butene, 1,3-butadiene, 1-pentene, 4-methyl-1-pentene, 1-hexene, 4-methyl-1-hexene, 1,4-hexadiene, 1,5-hexadiene, 1-octene, 1,6-octadiene, 1-nonene, 1-decene, 1,4-dodecadiene, 1-hexadecene, and 1-octadecene. Cyclic olefins and diolefins may also be used; such compounds include, for example, cyclopentene, 3-vinylcyclohexene, norbornene, 5-vinyl-2-norbornene, 5-ethylidene-2-norbornene, dicyclopentadiene, 4-vinylbenzocyclobutane, tetracyclododecane, dimethano-octahydronaphthalene, and 7-octenyl-9-borabicyclo-(3,3,1)nonane. Aromatic monomers that may be polymerized using the novel metallocenes include styrene, o-methylstyrene, m-methylstyrene, p-methylstyrene, p-tert-butylstyrene, m-chlorostyrene, p-chlorostyrene, p-fluorostyrene, indene, 4-vinylbiphenyl, acenaphthalene, vinylfluorene, vinylanthracene, vinylphenanthrene, vinylpyrene, and vinylchrisene.

Preparation of the Catalyst System:

In carrying out the present polymerization reaction, the transition metal complexes described herein as polymerization catalysts are preferably, although not necessarily, used in conjunction with a catalyst activator that converts the electronically neutral metal center of the complex to a cation, such that the complex is then cationic or zwiltterionic. Thus, it is preferred that prior to or upon polymerization, the transition metal complex selected as the polymerization catalyst is incorporated into a catalyst system that includes such an activator. Suitable catalyst activators are those that are typically referred to as ionic cocatalysts; such compounds include, for example, fluorohydrocarbylboron compounds such as tetra(pentafluorophenyl)borate, sodium tetrakis[(bis-3,5-trifluoromethyl)phenyl]borate, $H^+(OCH_2CH_3)_2[(bis-3,5-trifluoromethyl)$ -phenyl]borate, tritytetra(pentafluorophenyl)borate, and trifluoromethanesulfonate, and salts or acids of $BF_4^-$, $Ph_4B^-$ (Ph=phenyl), p-toluenesulfonate, $SbF_6^{31}$, and $PF_6^-$. Mixtures of activators may, if desired, be used.

For liquid phase or slurry polymerization, the catalyst and activator are generally mixed in the presence of inert diluents such as, for example, aliphatic or aromatic hydrocarbons, e.g., liquified ethane, propane, butane, isobutane, n-butane, n-hexane, isooctane, cyclohexane, methylcyclohexane, cyclopentane, methylcyclopentane, cycloheptane, methylcycloheptane, benzene, ethylbenzene, toluene, xylene, kerosene, Isopar® M, Isopar® E, and mixtures thereof. Liquid olefins, or the like, which serve as the monomers or comonomers in the polymerization process may also serve as the diluent; such olefins include, for example, ethylene, propylene, butene, 1-hexene, and the like. The amount of catalyst in the diluent will generally be in the range of about 0.01 to 1.0 mmoles/liter, with activator added such that the ratio of catalyst to activator is in the range of from about 10:1 to 1:2000, preferably in the range of from about 1:1 to about 1:200, on a molar basis.

Preparation of the catalyst/activator/diluent mixture is normally carried out under anhydrous conditions in the absence of oxygen, at temperatures in the range of from about –90° C. to about 300° C., preferably in the range of from about –10° C. to about 200° C.

The catalyst, activator and diluent are added to a suitable reaction vessel, in any order, although, as noted above, the catalyst and activator are usually mixed in the diluent and the mixture thus prepared then added to the reactor.

Polymerization:

Polymerization according to the invention is carried out by contacting the monomer(s), the catalyst, and the optional catalyst activator at a suitable temperature at reduced, elevated or atmospheric pressure, under an inert atmosphere, for a time effective to produce the desired polymer composition. The catalyst may be used as is or supported on a suitable support. In one embodiment, the transition metal complex is used as a homogeneous catalyst, i.e., as an unsupported catalyst, in a gas phase or liquid phase polymerization process. A solvent may, if desired, be employed. The reaction may be conducted under solution or slurry conditions, in a suspension using a perfluorinated hydrocarbon or similar liquid, in the gas phase, or in a solid phase powder polymerization.

Liquid phase polymerization generally involves contacting the monomer or monomers with the catalyst/activator mixture in the polymerization diluent, and allowing reaction to occur under polymerization conditions, i.e., for a time and at a temperature sufficient to produce the desired polymer product. Polymerization may be conducted under an inert atmosphere such as nitrogen, argon, or the like, or may be conducted under vacuum. Preferably, polymerization is conducted in an atmosphere wherein the partial pressure of reacting monomer is maximized. Liquid phase polymerization may be carried out at reduced, elevated or atmospheric pressures. In the absence of added solvent, i.e., when the olefinic monomer serves as the diluent, elevated pressures are preferred. Typically, high pressure polymerization in the absence of solvent is carried out at temperatures in the range of about 0° C. to about 300° C., preferably in the range of about 50° C. to about 200° C., and at pressures on the order of 1 to 5,000 atm, typically in the range of about 10 to 500 atm. When solvent is added, polymerization is generally conducted at temperatures in the range of about 0° C. to about 200° C., preferably in the range of about 50° C. to about 100° C., and at pressures on the order of 10 to 500 atm.

Polymerization may also take place in the gas phase, e.g., in a fluidized or stirred bed reactor, using temperatures in the range of approximately 60° C. to 120° C. and pressures in the range of approximately 10 to 1000 atm.

In gas and slurry phase polymerizations, the catalyst is used in a heterogeneous process, i.e., supported on an inert inorganic substrate. Conventional materials can be used for the support, and are typically particulate, porous materials; examples include oxides of silicon and aluminum, or halides of magnesium and aluminum. Particularly preferred supports from a commercial standpoint are silicon dioxide and magnesium dichloride.

The polyolefin resulting from the aforementioned reaction may be recovered by filtration or other suitable techniques. If desired, additives and adjuvants may be incorporated into the polymer composition prior to, during, or following polymerization; such compounds include, for example, pigments, antioxidants, lubricants, and plasticizers.

It is to be understood that while the invention has been described in conjunction with the preferred specific embodiments thereof, that the foregoing description as well as the examples that follow are intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

EXPERIMENTAL

All inorganic and organometallic reactions were conducted by using standard Schlenk and drybox techniques. Argon was purified by passage through columns of BASF R3-11 catalyst and 4-Å molecular sieves. Nitrogen was purified by passage through 4-Å molecular sieves. NMR spectra were recorded with a Varian Gemini 300 spectrometer.

Unless otherwise specified, all reagents were purchased from commercial suppliers and used without further purification. Ethylene was purified by passage through columns of BASF R3-11 catalyst and 4-Å molecular sieves. Toluene and heptane were purified by passage through columns of BASF R3-11 catalyst and 4-Å molecular sieves. Chlorobenzene was distilled under nitrogen from $P_2O_5$. Diethyl ether, butyl vinyl ether, and benzene-$d_6$ were dried over sodium/benzophenone and vacuum transferred. Methylene chloride-$d_2$ was dried over $CaH_2$ and vacuum-transferred. (1,5-COD) PdMeCl (1,5-COD=1,5-cyclooctadiene, Me=methyl) was prepared according to the literature procedure. Rulke et al. (1993) *Inorg. Chem.* 32:5769. The procedures to prepare representative complexes are described below.

In the following examples, the following convention is used for naming the ligands and catalyst. The N,N-diaryl-substituted diimine ligand diazabuta-1,3-diene is referred to as "DAD," while the N-aryl substituted pyridyl imine ligand is referred to as "pyim." Following "DAD" is an identification of the groups on the two carbon atoms of the diimine structure, in turn followed by the substitution on the aromatic group attached to each of the diimine nitrogen atoms. Thus, DAD(Me)(m-OH) refers to a ligand having the structure Ar—N=C(Me)-C(Me)=N—Ar wherein each Ar group is meta-substituted with a hydroxyl group. If the ligand is incorporated into a metal complex, the term for the ligand is followed by the metal and then by the anions, as in DAD(Me)(m-OH) $PdCl_2$. Analogous terminology is used to refer to the pyim ligands and complexes.

EXAMPLE 1

Representative Catalyst Synthesis

This example describes the synthesis of a palladium(II) catalyst containing an N,N-diaryl-substituted diimine ligand, with the aryl groups substituted with the Lewis acid substituent —$OSn(CH_3)_3$. The synthesis is illustrated in FIG. 1.

(a) Preparation of the Ligand Precursor m-aminomesitol:

A 250-mL round-bottomed flask was charged with 2,4,6-trimethylaniline (mesidine, 11.88 mL, 84.62 mmol) and 50 mL of pyridine. To this mixture, a solution of p-toluenesulfonyl chloride (16.13 g, 84.62 mmol) in pyridine (50 mL) was added, and the reaction mixture was stirred at room temperature for 17 h. The reaction mixture was poured into 800 mL of acidic ice water containing 125 ml of 37% HCl. The mixture was cooled to 0° C. for 3 h, and a yellow solid precipitated. The yellow solid was collected by filtration and dissolved in 18 L of 5% NaOH. To this solution, 1850 mL of 37% HCl was added until the mixture reached a pH of 5. The resulting white precipitate was collected and washed with 800 mL of water and then dried in vacuo to give N-(p-toluenesulfonyl)-2,4,6-trimethylaniline (N-(p-toluenesulfonyl)mesidine) (21.73 g, 89%). $^1$H NMR (300 MHz, $CDCl_3$): δ7.6 (d, 2H), 7.2 (d, 2H), 6.8 (s, 2H), 5.9 (s, 1H), 2.4 (s, 3H), 2.3 (s, 3H) 2.0 (s, 3H).

A 500-mL round-bottomed flask was charged with N-(p-toluenesulfonyl)mesidine (19.7 g, 67.9 mmol) as prepared above, 30 mL of acetic acid, and 400 mL of $CHCl_3$. The mixture was stirred for 5 min in order to dissolve the N-(p-toluenesulfonyl)mesidine. To this solution, $Pb(OAc)_4$ (32 g, 68.4 mmol) was added, and the reaction mixture was stirred at room temperature for 24 h. The resulting brown mixture was poured into 1 L of water, shaken vigorously, and then filtered through Celite to give a yellow filtrate. The filtrate was washed with 5% NaOH (aq, 3×150 mL) and evaporated to dryness to give a yellow solid. Recrystallization from 400 mL of hot EtOH afforded yellow needles of 3-acetoxy-N-p-toluenesulfonylmesidine (9.89 g, 42%). $^1$H NMR (300 MHz, DMSO-$d_6$): δ 7.8 (d, 2H), 7.4 (d, 2H), 6.8 (s, 1H), 5.9 (s, 1H), 2.4 (s, 3H), 2.1 (s, 3H), 1.85 (s, 3H), 1.80 (s, 3H), and 1.64 (s, 3H).

A 250-mL round-bottomed flask was charged with 50 mL of concentrated $H_2SO_4$ and cooled to −20° C. 3-Acetoxy-N-p-toluenesulfonylmesidine (9.89 g, 28.5 mmol) was added to the flask slowly over a 1 h period to give a brown solution. The solution was stirred at 0° C. for 8 h and stored at −25° C. for 16 h. The solution was poured into approximately 100 mL of ice and the resulting brownish-white mixture was stirred at room temperature for 3 h. The brown filtrate was collected by filtration through a glass frit and neutralized with approximately 120 mL of 28% ammonium hydroxide to a pH of 7. The mixture was then cooled to 10° C. for 16 h. An off-white precipitate was collected and dried in vacuo, and then extracted with 200 mL of $CHCl_3$. The brown extract was evaporated to give m-aminomesitol as a pale brown solid (1.62 g, 38%). $^1$H NMR (300 MHz, DMSO-$d_6$): δ 7.6 (s, 1H), 6.5 (s, 1H), 4.2 (s, 1H), 2.0 (s, 3H), 1.95 (s, 3H), and 1.94 (s, 3H).

(b) Synthesis of Ar—N=C(Me)-C(Me)=N—Ar, Ar=2,4,6-trimethyl-3-hydroxyphenyl ("DAD(Me)(m-OH)"; Compound 1):

A 100-mL Schlenk flask was charged with m-aminomesitol (700 mg, 4.63 mmol), 50 mL of methanol, and 0.24 mL of 88% formic acid. To this mixture, 2,3-butadione (0.20 mL, 2.3 mmol) was added via syringe, and the reaction mixture was stirred at reflux for 6 h and evaporated to dryness to give an orange solid 1. The solid was washed with 50 mL of dry pentane and dried in vacuo (0.61 g, 75%). $^1$H NMR (300 MHz, DMSO-$d_6$): δ 8.0 (s, 2H), 6.8 (s, 2H), 2.1 (s, 6H), 1.9 (s, 6H), and 1.8 (s, 6H). $^1$H NMR (300 MHz, $CD_2Cl_2$): δ 6.8 (s, 2H), 4.7 (br, 2H), 2.2 (s, 6H), 2.0 (s, 6H), and 1.9 (s, 6H).

(c) Synthesis of Ar—N=C(Me)-C(Me)=N—Ar, Ar=potassium 2,4,6-trimethyl-3-phenoxide ("DAD(Me)(m-O$^-$)(K$^+$)"; Compound 2):

To a red solution of 1 (299 mg, 0.848 mmol), a solution of $KN(SiMe_3)_2$ was added dropwise to give a heterogeneous yellow/brown mixture. The mixture was stirred at room temperature for 17 h. A yellow/brown solid was collected by filtration and washed with THF (3×3 mL) and then dried in vacuo. The yield was 405 mg, and the product 2 contained 0.6 equiv. of THF. $^1$H NMR (300 MHz, DMSO-$d_6$): δ 6.4 (s, 2H), 3.4 (m, 0.6 eq of THF), 1.9, 1.7, and 1.6 (overlapping s, totaling 24H), 1.8 (m, 0.6 eq of THF).

(d) Synthesis of Ar—N=C(Me)-C(Me)=N—Ar, Ar=(2,4,6-trimethyl-3-phenoxy)trimethyltin ("DAD(Me)(m-OSnMe$_3$)"; Compound 3):

A solution of trimethyltin chloride (74 mg, 0.371 mmol) in 5 mL of $Et_2O$ was added dropwise to a solution of 2 (80 mg, 0.186 mmol) in 5 mL of $Et_2O$, and the mixture was stirred at room temperature for 3 days. Within 3 h, the yellow solution had become a heterogeneous yellow mixture. A yellow/white solid 3 was collected by filtration and dried in vacuo (42 mg, 33%). $^1$H NMR (300 MHz, $CD_2Cl_2$): δ 6.8 (s, 2H), 2.1, 1.96, 1.9 and 1.8 (overlapping s, totaling 24H), 0.46 (s, 18).

(e) Synthesis of [Ar—N=C(Me)-C(Me)=N—Ar]PdMeCl, Ar=(2,4,6-trimethyl-3-phenoxy)trimethyltin ("DAD(Me)(m-OSnMe$_3$)PdMeCl"; Compound 4):

To a cold (−30° C.) solution of 3 (20 mg, 0.03 mmol) in 5 mL of $CH_2Cl_2$, a cold solution of (1,5-COD)PdMeCl (8 mg, 0.03 mmol) in 5 mL of $CH_2Cl_2$ was added dropwise. The reaction mixture was stirred at room temperature for 17 h. The mixture was evaporated to dryness to give an orange solid 4 (30 mg). $^1$H NMR(300 MHz, $CD_2Cl_2$): δ 6.92 and 6.88 (s, 2H), 5.6 and 2.4 (free COD), 2.15, 2.07, 2.01, 1.96, 1.93 (overlapping s, totaling 24H), 0.5 (s, 18H), 0.27 (s, 3 H).

EXAMPLE 2

Representative Catalyst Synthesis

Figure 2:
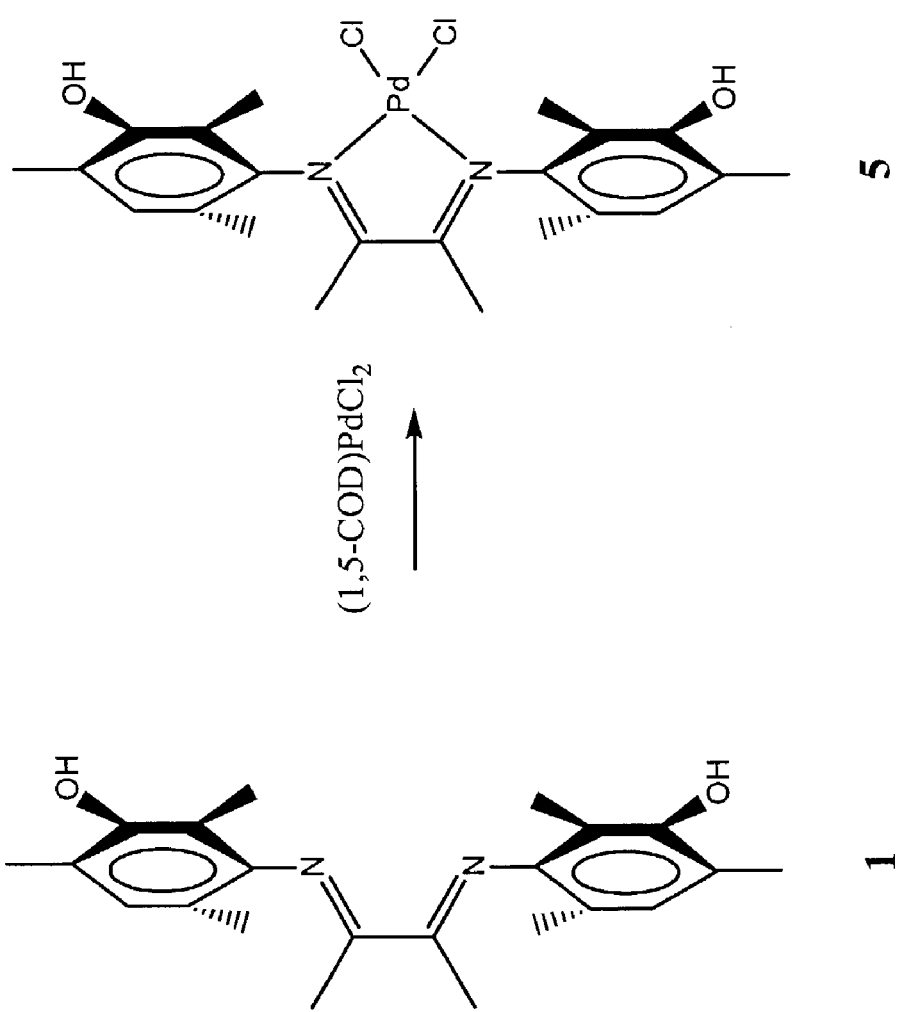
FIG. 2 schematically illustrates the synthesis of another representative Pd(II) catalyst of the invention, as described in Example 2.

Synthesis of [Ar—N═C(Me)-C(Me)═N—Ar]PdCl$_2$. Ar=2,4,6-trimethyl-3-hydroxyphenyl ("DAD(Me)(m-OH) PdCl$_2$"; Compound 5):

The referenced complex was synthesized using the reaction scheme illustrated in FIG. 2, as follows. A 20 mL vial was charged with 1, (1,5–COD)PdCl$_2$ (78 mg, 0.28 mmol), and 5 mL of THF, and the resulting orange slurry was stirred at room temperature for 16 h. The orange solid was collected on a frit and then suspended in CH$_2$Cl$_2$ (10 mL). The slurry was stirred for 1 h and then the orange powder was collected on a frit and dried in vacuo to give the product 5 (0.090 g, 61%). $^1$H NMR (300 MHz, THF-d$_8$): δ 7.27 (s, 2H), 6.81 (s, 2H), 2.19, 2.16, 2.15 (overlapping singlets, totaling 18H), 2.06 (s, 6H).

EXAMPLE 3

Representative Catalyst Synthesis

Figure 3:
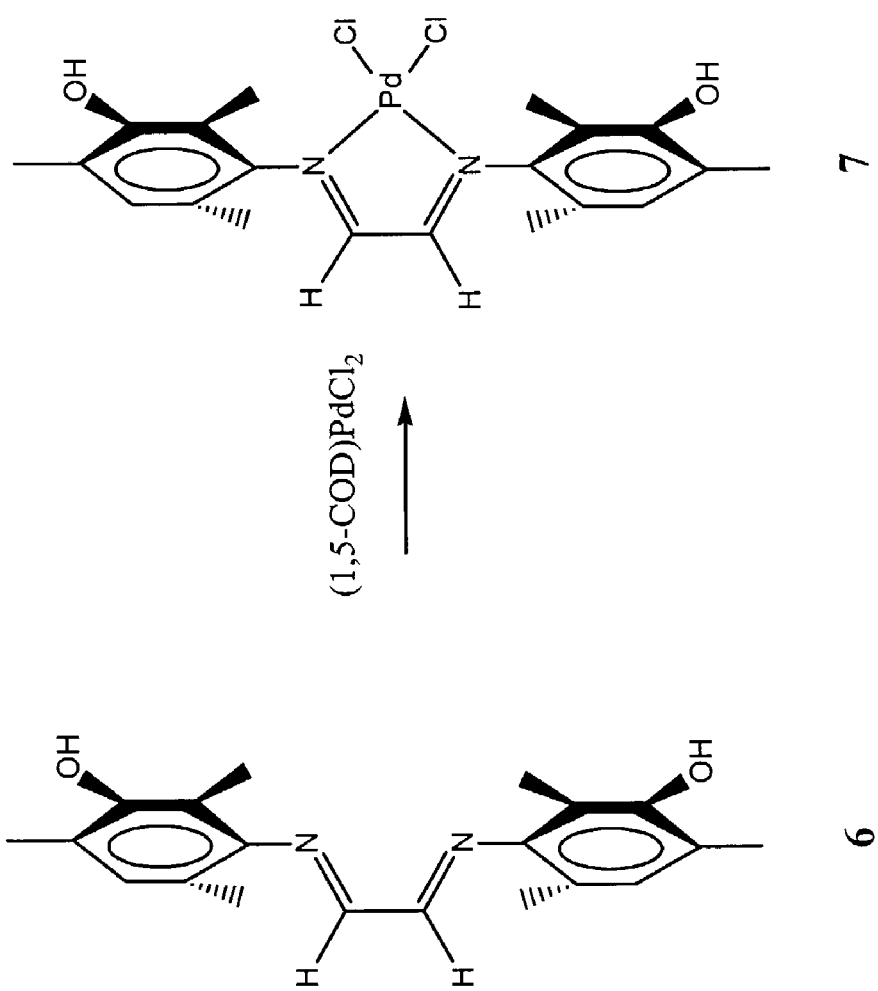
FIG. 3 schematically illustrates the synthesis of an analogous Pd(II) catalyst of the invention, wherein the adjacent carbon atoms of the α-diimine ligand are unsubstituted rather than substituted with methyl groups, as described in Example 3.

This example describes the synthesis of another palladium (II) complex suitable as a catalyst or catalyst precursor herein, as illustrated in FIG. 3.

(a) Synthesis of Ar—N═C(H)—C(H)═N—Ar, Ar=2,4, 6-trimethyl-3-hydroxyphenyl ("DAD(H)(m-OH)"; Compound 6):

To a solution of glyoxal (40 wt % aq., 70 mg, 0.482 mmol) in 5 mL of MeOH, a solution of m-aminomesitol (146 mg, 0.968 mmol) in 10 mL of MeOH was added. The resulting homogeneous orange/yellow mixture was stirred at room temperature for 17 h. The reaction mixture was evaporated and dried at 60° C. to give a yellow solid. Recrystallization from diethyl ether gave the desired product 6 as yellow needles (6 mg). The yellow filtrate was evaporated to dryness to give a yellow powder (118 mg). The products were combined to give a total yield of 124 mg (78%). $^1$H NMR (300 MHz, CDCl$_3$): δ 8.0 (s, 2), 6.9 (s, 2, H), 4.7 (s, 2), 2.2, 2.07, and 2.06 (all s, totaling 18H).

(b) Synthesis of [Ar—N═C(H)—C(H)═N—Ar]PdCl$_2$, Ar=2,4,6-trimethyl-3-hydroxyphenyl ("DAD(H)(m-OH) PdCl$_2$"; Compound 7):

A 20 mL vial was charged with 6 (95 mg, 0.286 mmol), (1,5-COD)PdCl$_2$ (81 mg, 0.284 mmol), and 10 mL of CH$_2$Cl$_2$. After being stirred at room temperature for 3 d, the mixture changed from a yellow solution to brown slurry. The brown solid was collected on a glass frit, washed with CH$_2$Cl$_2$ and then dried in vacuo to give a brown powder (104 mg, 73%). $^1$H NMR (300 MHz, DMSO): δ 8.33 (s, 2H), 8.17 (s, 2H), 6.82 (s, 2H), 2.18 (s, 6H), 2.17 (s, 6H), 2.14 (s, 6H).

EXAMPLE 4

Representative Catalyst Synthesis

Figure 4:
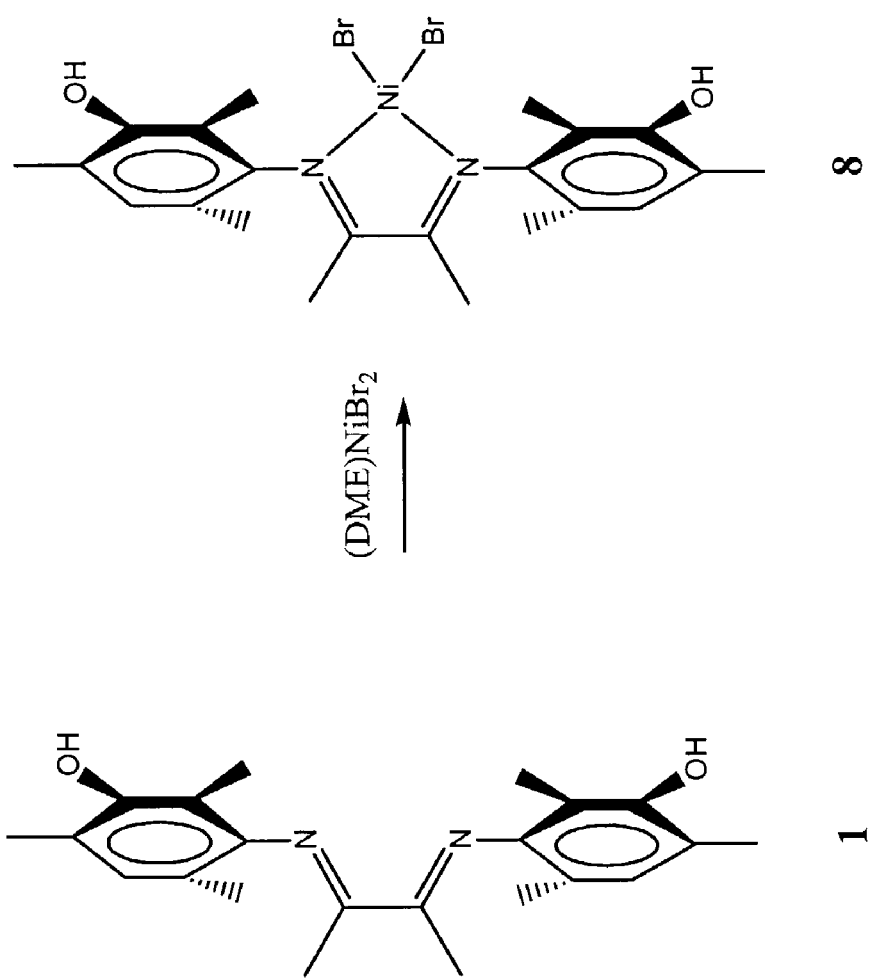
FIG. 4 schematically illustrates the synthesis of a representative Ni(II) catalyst of the invention, wherein an α-diimine ligand is substituted with hydroxyl groups, as described in Example 4.

Synthesis of [Ar—N═C(Me)-C(Me)═N—Ar]NiBr$_2$, Ar=2,4,6-trimethyl-3-hydroxyphenyl ("DAD(Me)(m-OH) NiBr$_2$"; Compound 8):

The referenced complex was synthesized using the reaction scheme illustrated in FIG. 4, as follows. A 20-mL vial was charged with 1 (50 mg, 0.14 mmol), (DME)NiBr$_2$ (DME=1,2-dimethoxyethane) (42 mg, 0.14 mmol), and 5 mL of THF and the brown slurry was stirred at room temperature for 16 h. The brown solid was collected on a frit, washed with CH$_2$Cl$_2$ (10 mL), and then dried in vacuo to give 8 (0.038 g, 48%).

EXAMPLE 5

Representative Catalyst Synthesis

Figure 5:
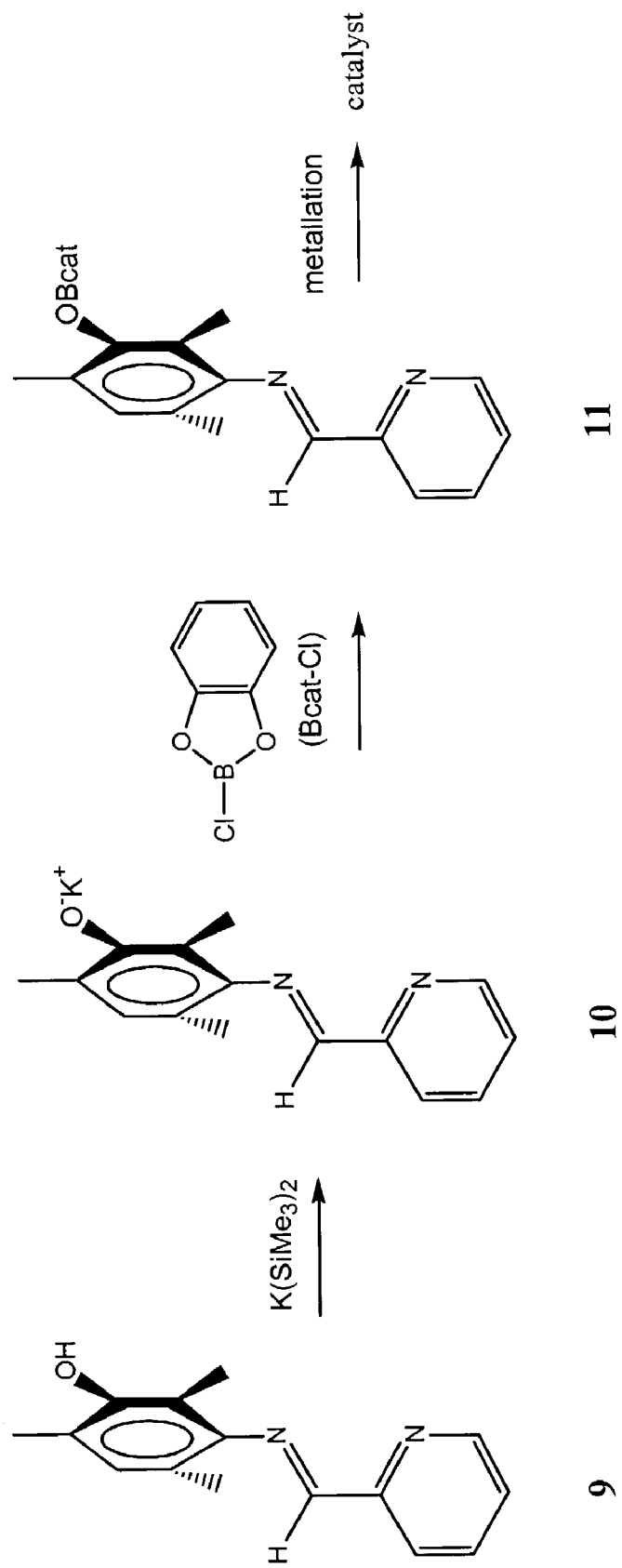
FIG. 5 schematically illustrates the synthesis of another representative catalyst of the invention, wherein a pyridyl imine ligand is substituted with an —O-catecholborane stabilizing group, as described in Example 5.

This example describes the synthesis of a transition metal complex containing a pyridyl imine ("pyim") ligand, as illustrated in FIG. 5.

(a) Synthesis of Ar—N═C(H)-2-pyridine, Ar=2,4,6-trimethyl-3-hydroxyphenyl ("pyim(m-OH)"; Compound 9):

A 250-mL round bottomed flask was charged with 3-amino-2,4,6-trimethylphenol (0.96 g, 6.3 mmol), pyridine carboxaldehyde (0.68 g, 6.3 mmol), and methanol (75 mL). The mixture was stirred for 16 h. The yellow solution was evaporated to dryness. The solid was washed with toluene (2×10 mL) and dried in vacuo to give a yellow powder 9 (1.4 g, 91%). $^1$H NMR (CD$_2$Cl$_2$): δ 8.69 (d, 1H), 8.27 (d, 1H), 8.24 (s, 1H), 7.85 (t, 1H), 7.41 (dd, 1H), 6.84 (s, 1H), 4.92 (br, 1H), 2.21 (s, 3H), 2.04 (s, 3H), 2.03 (s, 3H).

(b) Synthesis of Ar—N═C(H)-2-pyridine, Ar=potassium 2,4,6-trimethyl-3-phenoxide ("pyim(m-O$^-$)(K$^+$)"; Compound 10):

A vial was charged with 9 (0.25 g, 1.03 mmol) and diethyl ether (5 mL). Potassium hexamethyldisilazide (0.206 g, 1.03 mmol) in diethyl ether (5 mL) was added and the mixture became an orange slurry. The solution was stirred for 2 h and then cooled to −30° C. The orange solid was collected on a glass frit and was dried in vacuo (0.254 g, 88%). $^1$H NMR (300 MHz, DMSO): δ 8.65 (d, 1H), 8.16 (d, 1H), 8.08 (s, 1H), 7.91 (t, 1H), 7.45 (m, 1H), 6.41 (s, 1H), 1.90 (s, 3H) 1.87 (s, 3H), 1.78 (s, 3H).

(c) Synthesis of Ar—N═C(H)-2-pyridine, Ar=B-(2,4,6-trimethyl-3-phenoxy) Catecholborane ("pyim(m-OBcat"); Compound 11):

A vial was charged with 10 (0.131 g, 0.47 mmol) and CH$_2$Cl$_2$ (5 mL) and cooled to −30° C. A cold (−30° C.) solution of B-chlorocatecholborane (0.072 g, 0.47 mmol) in CH$_2$Cl$_2$)5 mL) was added and the mixture turned from a red-orange slurry to a tan solution. The mixture was warmed to room temperature and stirred for 1 h and then evaporated to dryness to give a yellow solid. The solid was extracted with CH$_2$Cl$_2$, filtered through Celite, and then evaporated to dryness to give a yellow-green powder 11, which was stored at −30° C. due to thermal sensitivity (0.138 g, 82%). $^1$H NMR (300 MHz, CD$_2$Cl$_2$): δ 8.74 (d, 1H), 8.50 (s, 1H), 8.37 (d, 1H), 7.98 (t, 1H), 7.52 (t, 1H), 7.13 (m, 2H), 7.06 (m, 2H), 7.00 (s, 1H), 2.22 (s, 3H) 2.15 (s, 3H), 2.06, (s, 3H.

(d) Metallation of 11:

Ligand 11 prepared in the preceding section maybe metallated using any suitable metallation reagents and the procedures described herein. Preferred palladium reagents include (1,5-COD)PdMeCl, (1,5-COD)PdCl$_2$, (1,5-COD) PdMe$_2$, and (1,5-COD)Pd(CH$_2$SiMe$_3$)$_2$, while a preferred nickel reagent is (DME)NiBr$_2$, and a preferred zinc reagent is an aryloxyethylzinc compound such as phenoxyethylzinc (EtZnOPh). (1,5-COD)PdMeCl, (1,5-COD)PdCl$_2$, and (DME)NiBr$_2$ may be obtained commercially, and synthesis of (1,5-COD)Pd(CH$_2$SiMe$_3$)$_2$ is described infra, in Example 8. The other metallation reagents were synthesized as follows:

(1,5-COD)PdMe$_2$: A 100-mL Schlenk flask was charged with (1,5-COD)PdMeCl (263 mg, 0.996 mmol) and diethyl ether (30 mL), and then cooled to −78° C. Methylmagnesium bromide (0.8 mL of a 1.5 M toluene/THF solution, 1.2 mmol) was added dropwise and the reaction mixture was stirred at −78° C. for 3 h. The solvent was removed at −30° C. to give an off-white solid. The solid was extracted with cold pentane (−30° C., 3×30 mL), and the extract was filtered through a Celite to give a colorless liquid. The liquid was evaporated at −30° C. to give an off-white powder (73 mg, 30%).

EtZnOPh: In the drybox, a 100-mL Schlenk flask was charged with $Et_2O$ (30 mL) and cooled to −78° C. Diethylzinc (9.0 mL of a 1.0 M hexane solution, 9.0 mmol) was added via syringe. A solution of phenol (0.847 g of phenol in 10 mL of $Et_2O$) was added to the Schlenk flask, and the colorless reaction mixture was stirred at −78° C. for 1 h. The mixture was evaporated to give a white solid (1.593 g, 94%). $^1$H NMR (300 MHz, DMSO-$d_6$): δ 7.1, 6.6 (m, 5H), 1.2 (t, 3H), 0.1 (m, 2H).

EXAMPLE 6

Representative Catalyst Synthesis

Figure 6:
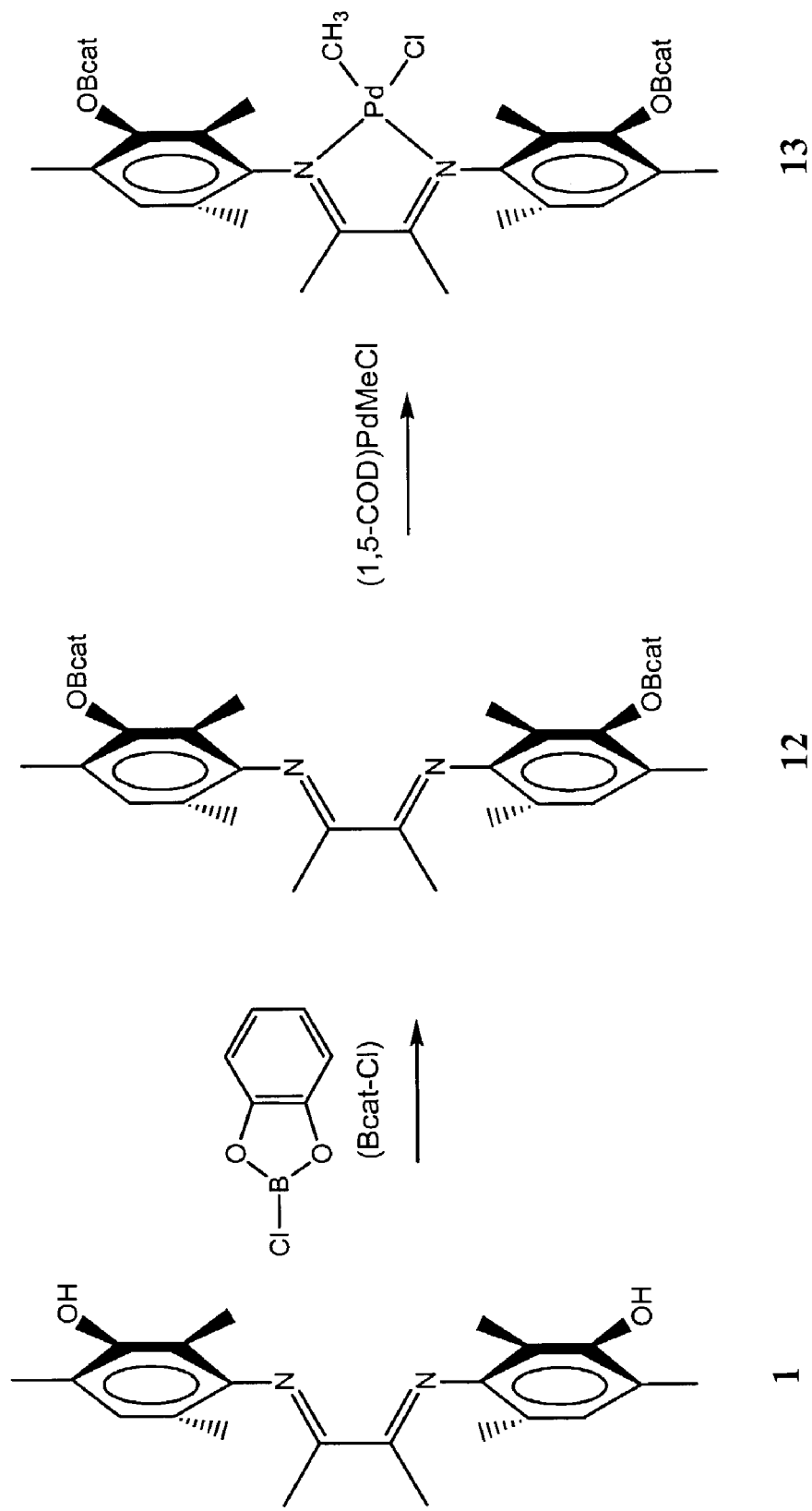
FIG. 6 schematically illustrates the synthesis of a Pd(II) catalyst in which an α-diimine ligand is substituted with —O-catecholborane stabilizing groups, as described in Example 6.

Synthesis of [Ar—N═C(Me)-C(Me)═N—Ar]PdMeCl, Ar=2,4,6-(trimethyl-3-catecholborane) ("DAD(Me)(m-O-Bcat)PdMeCl"; Compound 13):

The referenced complex was synthesized using the reaction scheme illustrated in FIG. 6, as follows. The catalyst was prepared from compound 1 by reaction with B-chlorocatecholborane as described in part (c) of Example 5, to give the borane-substituted ligand 12 (Ar—N═C(Me)-C (Me)═N—Ar, Ar=2,4,6-(trimethyl-3-catecholborane) ("DAD(Me)(O-Bcat)"). The product was isolated as described in the preceding example, and then metallated using (1,5-COD)PdMeCl as described in part (e) of Example 1, to give the desired product 13.

EXAMPLE 7

Representative Catalyst Synthesis

Figure 7:
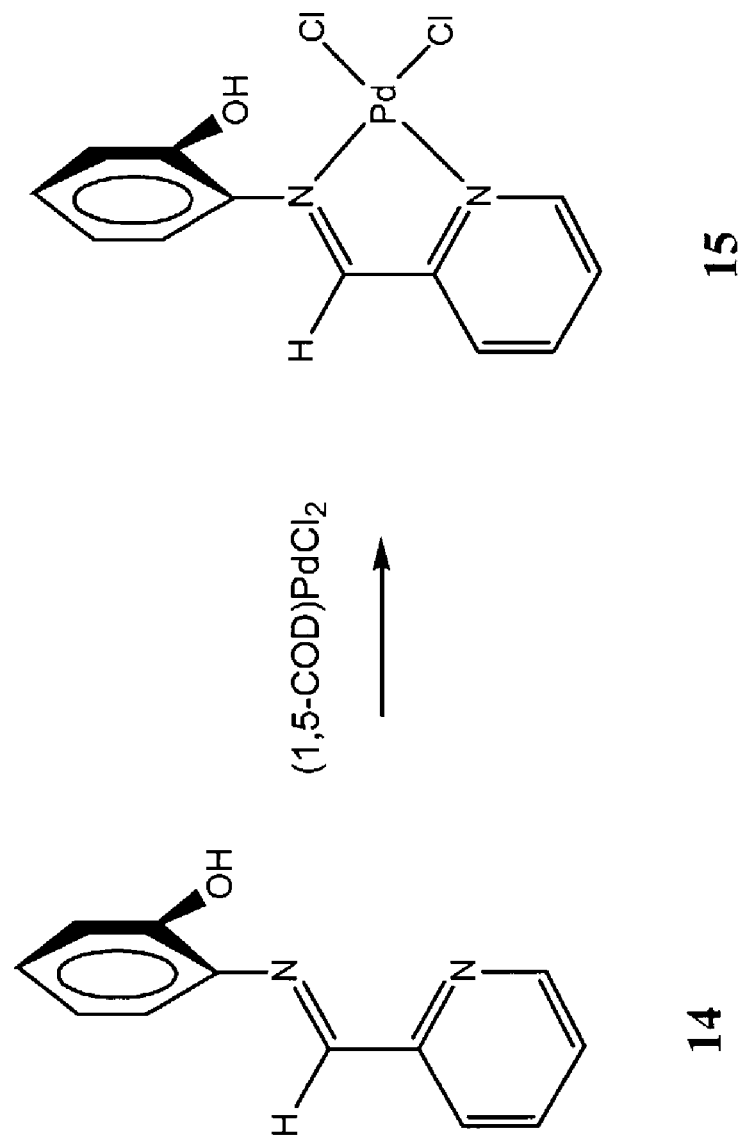
FIG. 7 schematically illustrates the synthesis of a Pd(II) catalyst of the invention containing a hydroxyl-substituted pyridyl imine ligand, as described in Example 7.

This example describes the synthesis of another transition metal complex containing a pyridyl imine ("pyim") ligand, as illustrated in FIG. 7.

(a) Synthesis of Ar—N═C(H)-2-pyridine, Ar=2-hydroxyphenyl ("pyim(o-OH)"; Compound 14):

A 250-mL round bottomed flask was charged with 2-aminophenol (3.15 g, 28.9 mmol), 2-pyridine carboxaldehyde (3.14 g, 29.3 mmol), and methanol (75 mL). The mixture was stirred for 15 h and then was evaporated to dryness to give 14 as a tan solid (5.20 g, 91%). $^1$H NMR (CD$_2$Cl$_2$): δ 8.84 (s, 1H), 8.70 (br, 1H), 8.18 (d, 1H), 7.80 (t, 1H), 7.62 (br, 1H), 7.39 (m, 2 H), 7.25 (t, 1H), 7.04 (d, 1H), 6.95 (t, 1H).

(b) [Ar—N═C(H)-2-pyridine]PdCl$_2$, Ar=2-hydroxyphenyl ("pyim(o-OH)PdCl$_2$"; Compound 15):

In the drybox, 20-mL vial was charged with 14 (0.20 g, 1.0 mmol), (1,5-COD)PdCl$_2$ (0.29 g, 1.0 mmol) and CH$_2$Cl$_2$ (10 mL). The mixture was stirred for 24 h and the solution was decanted away from a tan precipitate. The solid was washed with toluene (2×5 mL) and dried in vacuo to give 15 as a tan powder (0.30 g, 79%). $^1$H NMR (DMSO-$d_6$): δ 10.05 (br, 1H), 9.05 (d, 1H), 8.73 (s, 1H), 8.39 (t, 1H), 8.20 (d, 1H), 7.97 (t, 1H), 7.19 (m, 2H), 6.92 (d, 1H), 6.83 (t, 1H).

EXAMPLE 8

Representative Catalyst Synthesis

Figure 8:
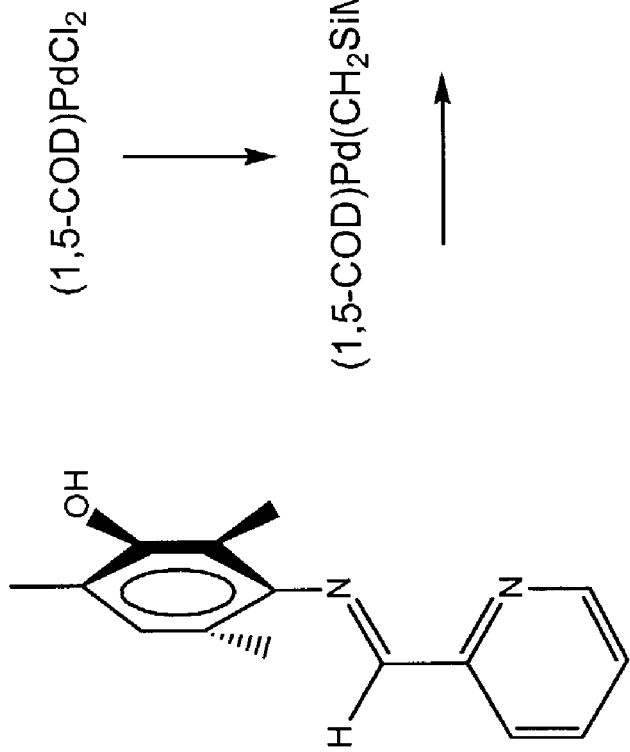
FIG. 8 schematically illustrates the synthesis of a similar Pd(II) catalyst of the invention, but wherein the univalent ligands are —$CH_2$—$Si(CH_3)_3$ groups, as described in Example 8.
Figure 8:
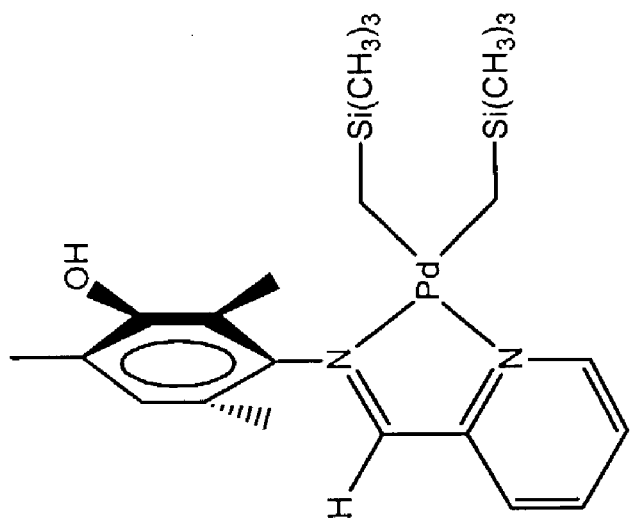

This example describes the synthesis of another transition metal complex containing a pyridyl imine ("pyim") ligand, as illustrated in FIG. 8.

(a) Synthesis of the Metallation Reagent (1,5-COD)Pd(CH$_2$SiMe$_3$)$_2$ (Compound 16):

A 100-mL Schlenk flask was charged with (1,5-COD) PdCl$_2$ (200 mg, 0.701 mmol) and 30 mL of Et$_2$O, and was cooled at −78° C. Trimethylsilylmethyllithium (1.4 mL of a 1 M pentane solution, 1.4 mmol) was diluted with Et$_2$O (10 mL). The resulting solution was added to the Schlenk flask by cannula and the reaction mixture was stirred at −78° C. for 1.5 h. The solvent was then removed at −30° C. to give 16 as a brown solid (74 mg, 27%). $^1$H NMR (300 MHz, C$_6$D$_6$): δ 5.1 (m, 4H), 1.9 (m, 8H), 0.8 (s, 4H), 0.3 (s, 18H).

(b) Synthesis of [Ar—N═C(H)-2-pyridine]Pd (CH$_2$SiMe$_3$)$_2$, Ar=2,4,6-trimethyl-3-hydroxyphenyl ("pyim (m-OH)Pd(CH$_2$SiMe$_3$)$_2$"; Compound 17):

In the drybox, a 100-mL round bottomed flask was charged with 16 (0.30 g, 0.77 mmol) and diethyl ether (15 mL). The mixture was cooled to −30° C. and then ligand 9 (0.19 g, 0.77 mmol), synthesized as described in part (a) of Example 5, was added dropwise as a solution in diethyl ether (5 mL). The mixture was warmed to room temperature and then turned dark red. The mixture was stirred for 2 h and then evaporated to dryness to give a red, oily solid. The solid was dissolved in heptane (10 mL) and filtered through Celite and then evaporated to dryness. The solid was recrystallized from heptane to give red crystals (multiple fractions, 0.98 g, 25%). $^1$H NMR (CD$_2$Cl$_2$): δ 8.82 (d, 1H), 8.32 (s, 1H), 8.04 (t, 1H), 7.70 (m, 2H), 6.91 (s, 1H), 4.80 (br, 1H), 2.25 (s, 3H), 2.16 (s, 6H), 0.19 (s, 2H), −0.03 (s, 9H), −0.22 (s, 9H), −0.30 (s, 2H).

EXAMPLE 9

Representative Catalyst Synthesis

Figure 9:
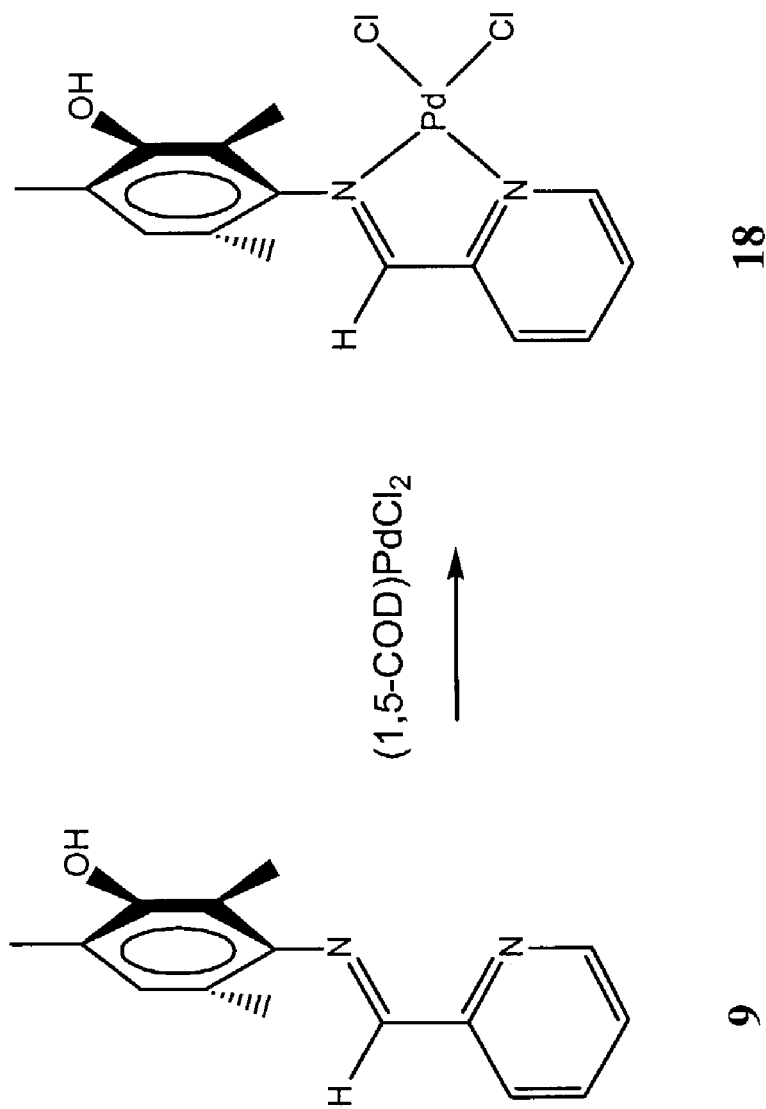
FIG. 9 schematically illustrates the synthesis of a similar Pd(II) catalyst of the invention, but wherein each univalent ligand is a chlorine atom, as described in Example 9.

Synthesis of [Ar—N═C(H)-2-pyridine]PdCl$_2$, Ar=2,4,6-trimethyl-3-hydroxyphenyl ("pyim(m-OH)PdCl$_2$" Compound 18):

The referenced complex was synthesized using the reaction scheme illustrated in FIG. 9, as follows. In the drybox, a 20-mL vial was charged with ligand 9, synthesized as described in part (a) of Example 5, (0.200 g, 0.825 mmol), (1,5-COD)PdCl$_2$ (0.235 g, 0.823 mmol), and CH$_2$Cl$_2$ (10 mL). The mixture turned orange with an orange precipitate. The slurry was stirred for 16 h and then evaporated to dryness to give a yellow powder. The powder was washed with toluene (2×10 mL) and CH$_2$Cl$_2$ (10 mL). The powder was collected on a glass frit and dried in vacuo to give 18 (0.277 g, 80%). $^1$H NMR (DMSO-$d_6$): δ 9.06 (d, 1H), 8.59 (s, 1H), 8.42 (t, 1 H), 8.32 (s, 1H), 8.16 (d, 1H), 7.99 (t, 1H), 6.82 (s, 1H), 2.14 (s, 6H), 2.12 (s, 3H).

EXAMPLE 10

Polymerization Using a Pd/Sn Catalyst of the Invention

Figure 10:
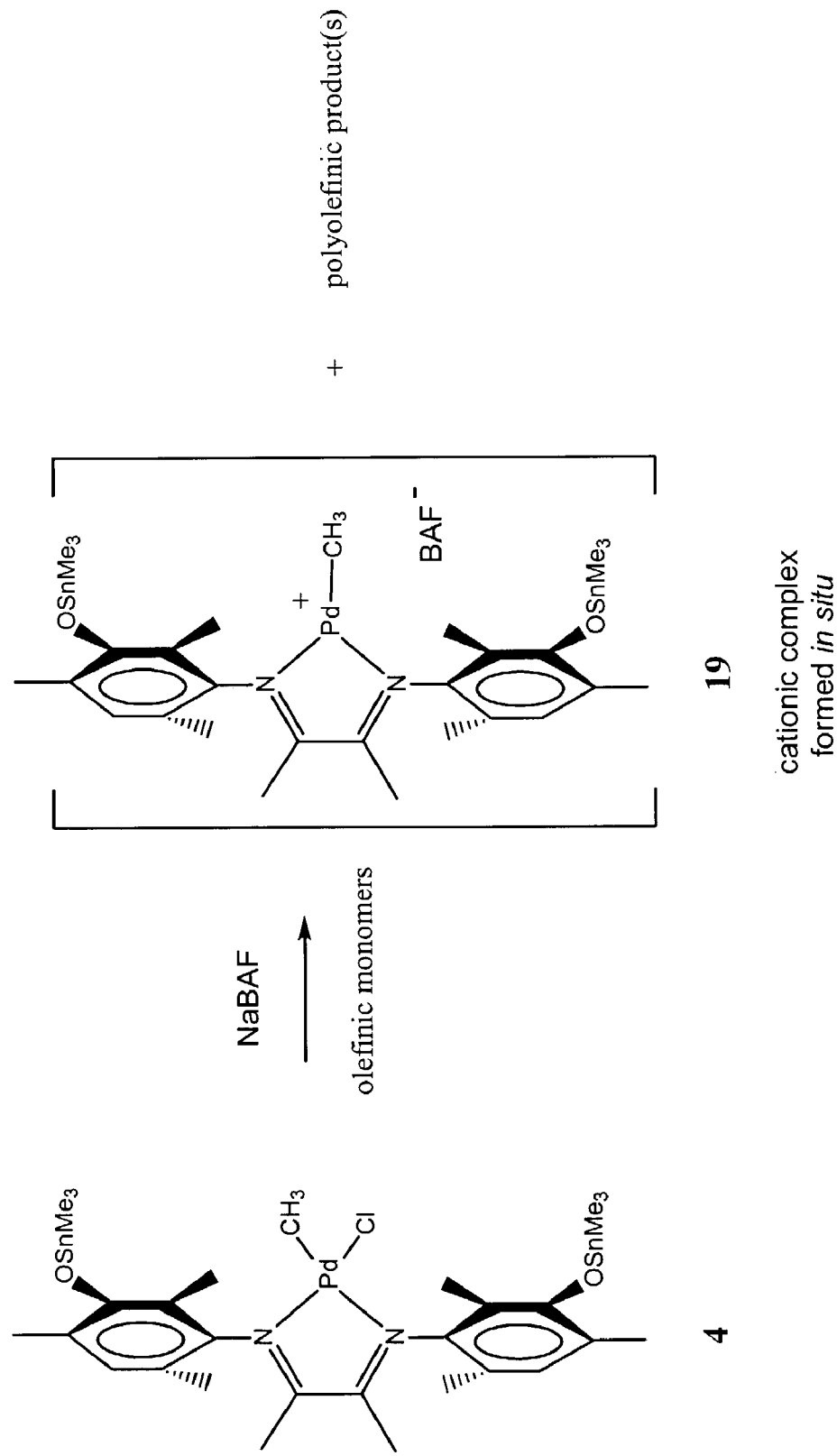
FIG. 10 schematically illustrates the olefin polymerization reaction of Example 10, wherein a cationic Pd(II)/Sn complex is used as the polymerization catalyst.
Figure 11:
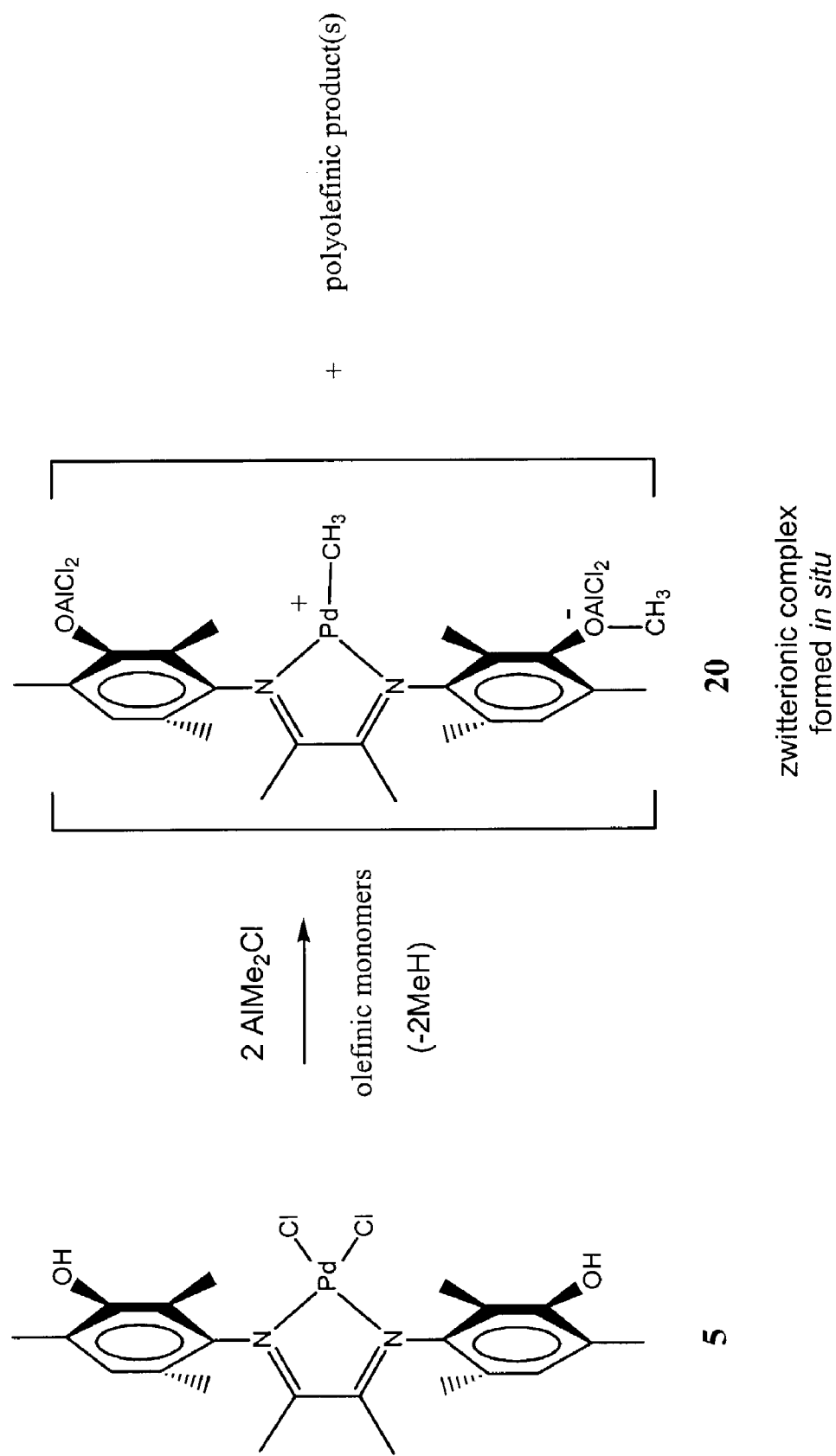
FIG. 11 schematically illustrates the olefin polymerization reaction of Example 11, wherein a zwitterionic Pd(II)/Al complex is used as the polymerization catalyst.

The following general procedure was used in the polymerization of olefinic monomers using DAD(Me)(m-OSnMe$_3$)Pd-BAF 19 as a polymerization catalyst, as illustrated in FIG. 10: Methylene chloride (150 mL) was placed in a 300-mL glass reactor, which was then flushed and charged with ethylene to a pressure of 15 psig. The solution was allowed to equilibrate at room temperature for 15 min, and then a solution of catalyst 4 (approximately 0.01 mmol), synthesized as described in Example 1, and polar monomer in $CH_2Cl_2$ (10 mL) was added. A solution of NaBAF (1 eq) in $CH_2Cl_2$ (10 mL) was injected into the reactor with argon overpressure to form the active catalyst 19 in situ and initiate polymerization. After the desired time period, an aliquot was removed and evaporated to dryness. The sample was weighed and analyzed by $^1H$ NMR. When the selected monomers were ethylene and BVE, the NMR spectrum confirmed the presence of polyethylene in the product, and the catalyst was found to have a surprising tolerance to relatively low concentrations of BVE compared to that observed with the parent Brookhart catalyst (DAD(Me)Pd-BAF). The same was observed when ethylene and vinyl acetate were selected as the monomeric reactants.

EXAMPLE 11

Polymerization Using a Zwitterionic Pd/Al Catalyst of the Invention

The following general procedure was used in the polymerization of olefinic monomers using DAD(Me)(m-OAlMe$_2$)Pd-zwit 20 as a polymerization catalyst: In the drybox, a 20-mL vial was charged with 1-hexene (0.7 g), catalyst 5 (0.004 g), synthesized as described in Example 2, and toluene (2 mL). The slurry was stirred and AlMe$_2$Cl (15 µL, 2 eq) was added by syringe, forming catalyst 20 in situ. The mixture became yellow and homogeneous. Polar monomer (0.2 g) was added and the mixture was stirred for 16 h and then evaporated to dryness. The resulting polymer was weighed and analyzed by $^1H$ NMR. In some cases, the polymer was redissolved in toluene and precipitated with acetone before NMR analysis.

When the selected monomers were 1-hexene and BVE, the NMR spectrum confirmed the presence of polyhexene and poly(BVE) in the product.

EXAMPLE 12

Polymerization Using a Cationic Pd/Al Catalyst of the Invention

Figure 12:
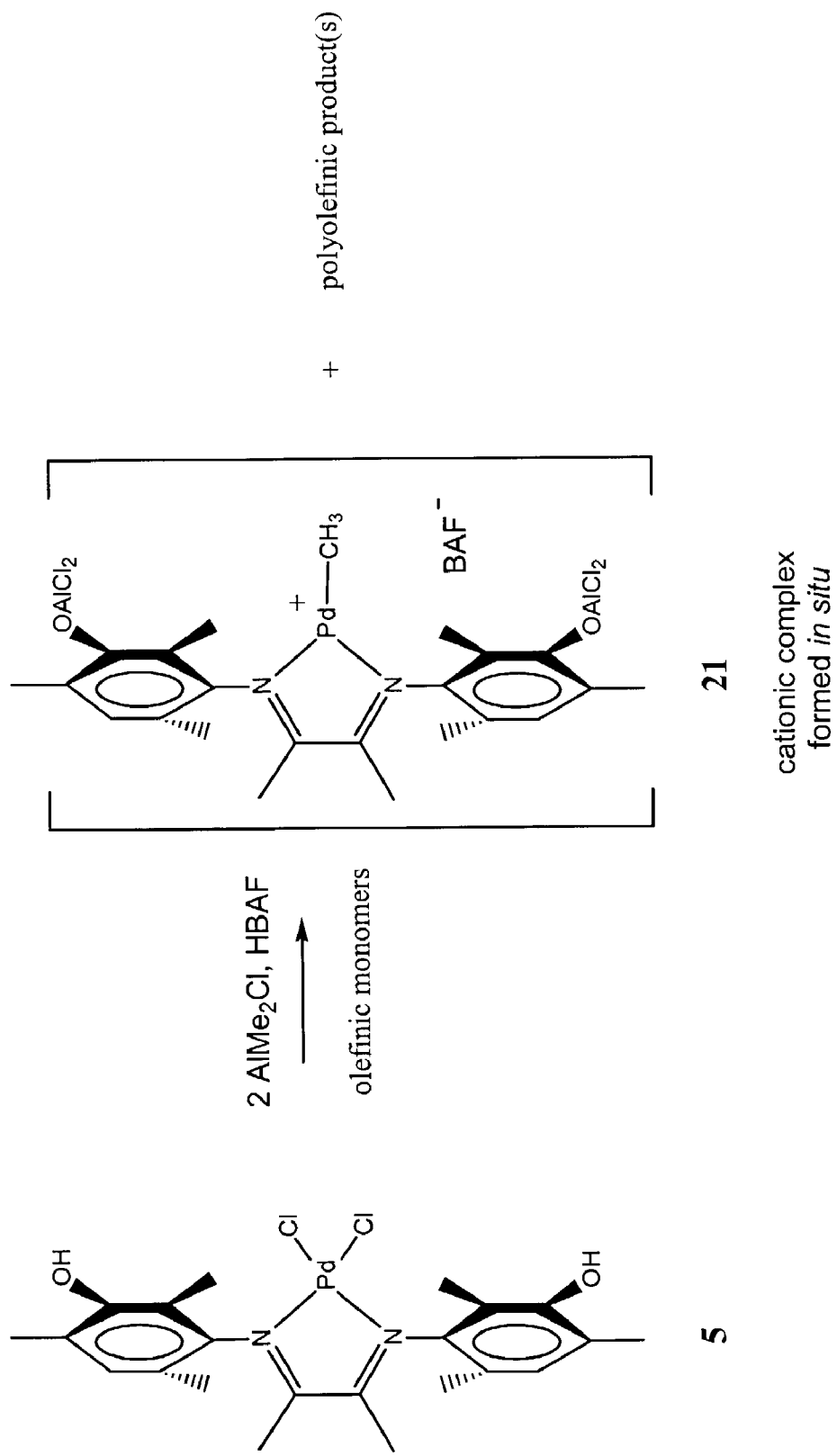
FIG. 12 schematically illustrates the olefin polymerization reaction of Example 12, wherein a cationic Pd(II)/Al complex is used as the polymerization catalyst.

The following general procedure was used in the polymerization of olefinic monomers using DAD(Me)(m-OAlMe$_2$)Pd-BAF 21 as a polymerization catalyst, as illustrated in FIG. 12: In the drybox, a 20-mL vial was charged with 1-hexene (0.7 g), compound 5 (0.004 g), and toluene (2 mL). The slurry was stirred and AlMe$_2$Cl (15 µL, 2 eq) was added by syringe. The mixture became yellow and homogeneous. After 5 min, HBAF (0.008 g, 1 eq) was added and the mixture turned red-brown, forming catalyst 21 in situ. After an additional 5 min, polar monomer (0.2 g) was added and the mixture was stirred for 16 h and then evaporated to dryness. The resulting polymer was weighed and analyzed by $^1H$ NMR. The NMR spectrum confirmed the presence of polyhexene and poly(BVE) in the product, as was the case for the zwitterionic Pd/Al catalysts used in the polymerization reaction of Example 11.

EXAMPLE 13

Polymerization Using a Zwitterionic Ni/Al Catalyst of the Invention

Figure 13:
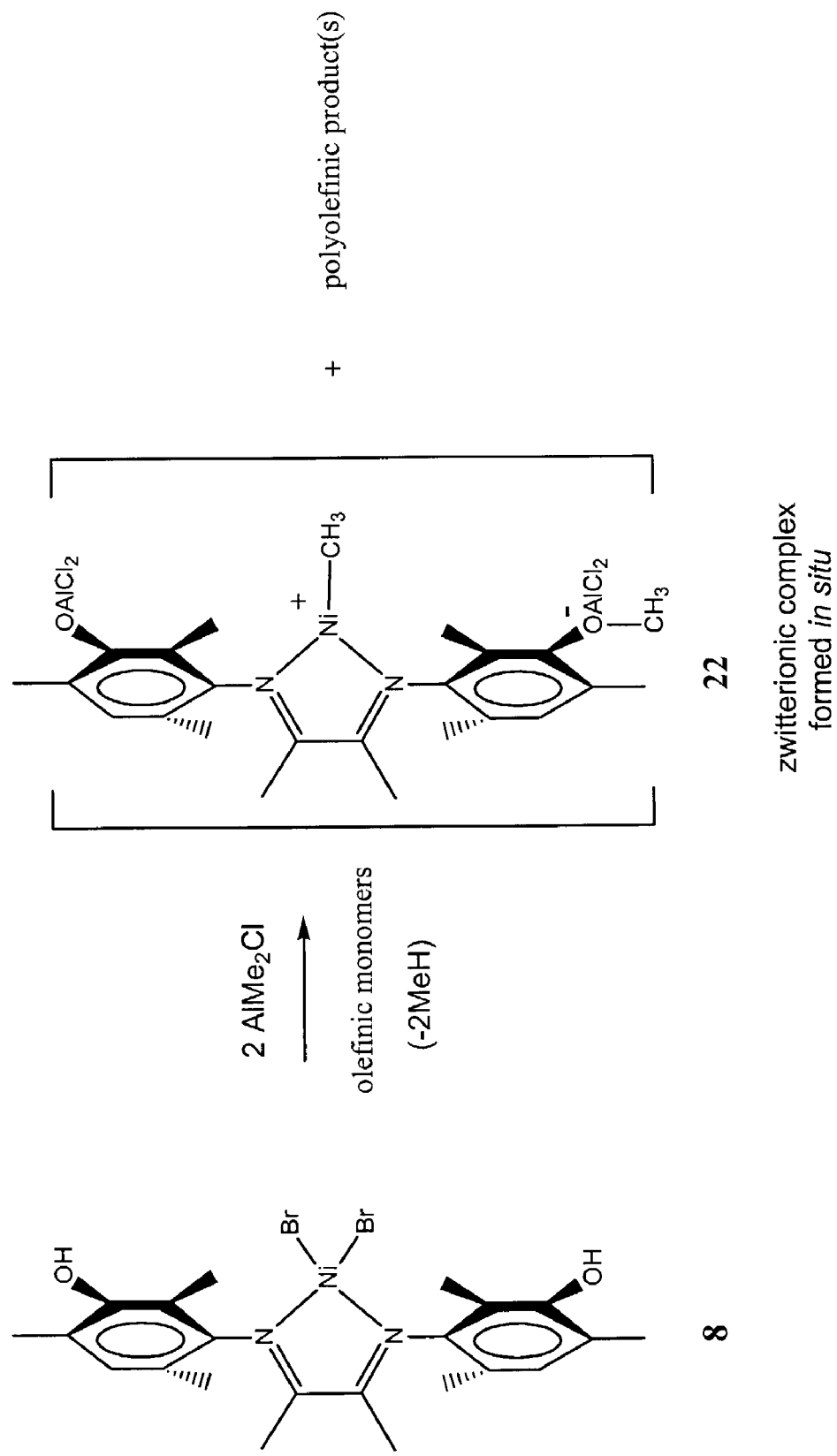
FIG. 13 schematically illustrates the olefin polymerization reaction of Example 13, wherein a zwitterionic Ni(II)/Al complex is used as the polymerization catalyst.

The procedure of Example 11 was repeated using DAD (Me)(m-OAlMe$_2$)Ni-zwit 22 as a polymerization catalyst, as illustrated in FIG. 13: In this example, catalyst 8 was used in lieu of catalyst 5. It will be appreciated that upon addition of AlMe$_2$Cl to the reactor, the active catalyst 22 forms in situ. The resulting polymeric product was weighed and analyzed by $^1H$ NMR. The NMR spectrum confirmed the presence of polyhexene and poly(BVE) in the product, as was the case for the zwitterionic Pd/Al catalysts used in the polymerization reaction of Example 11.

EXAMPLE 14

Polymerization Using a Cationic Ni/Al Catalyst of the Invention

Figure 14:
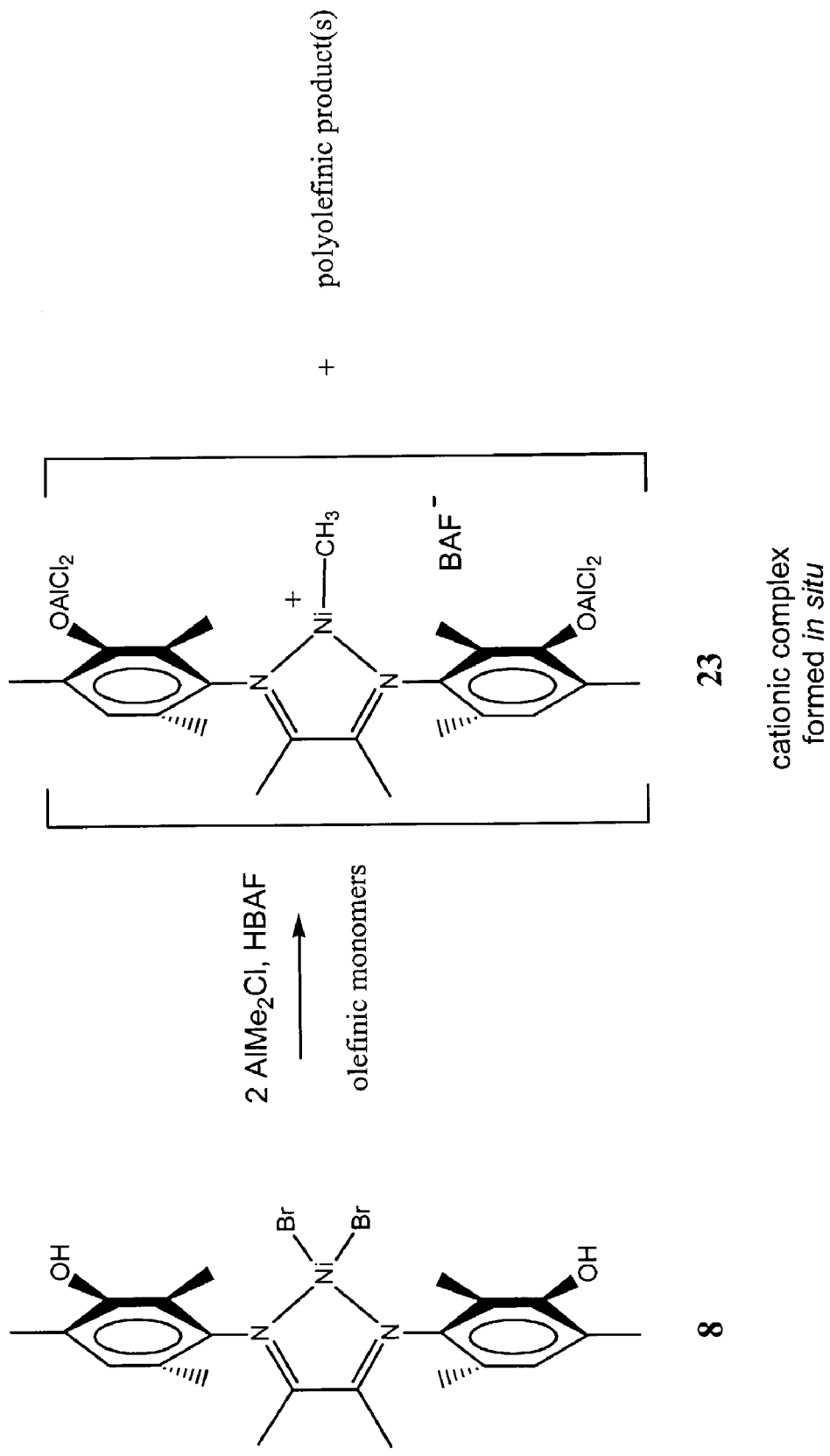
FIG. 14 schematically illustrates the olefin polymerization reaction of Example 14, wherein a cationic Ni(II)/Al complex is used as the polymerization catalyst.

The procedure of Example 12 was repeated using DAD (Me)(m-OAlMe$_2$)Ni-BAF 23 as a polymerization catalyst, as illustrated in FIG. 14: In this example, catalyst 8 is used in lieu of catalyst 5. It will be appreciated that upon addition of AlMe$_2$Cl and HBAF to the reactor, the active catalyst 23 forms in situ. The $^1H$ NMR spectrum confirmed the presence of polyhexene and poly(BVE) in the product.

We claim:

1. A method for preparing a polyolefin substituted with pendant functional groups, comprising contacting, under polymerization conditions, (a) a functionalized olefinic monomer composed of an olefin directly or indirectly substituted on an olefinic carbon atom with a polar, electron-donating functional group, with (b) a catalytically effective amount of a transition metal complex having the structure of formula (I) and (c) an activator that converts the transition metal complex, to an ionic or zwitterionic catalyst which facilitates stepwise polymer synthesis by successive insertion reactions of olefinic monomers, the ionic or zwitterionic catalyst having the structure of formula (Ia)

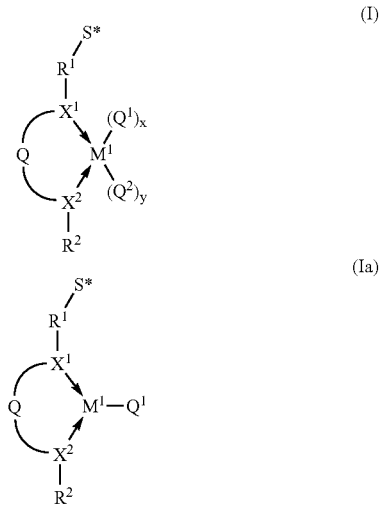

wherein:
M$^1$ is a transition metal selected from Pd(II), Fe(II), Co(II), Ni(II), V(IV), Zr(IV), Hf(IV), Ti(IV), Ru(II), Rh(II), Os(II), Ir(II), or Pt(II);

x and y are integers in the range of zero to w, and the sum of x and y is w;

$X^1$ and $X^2$ are heteroatoms coordinated to $M^1$;

$R^1$ is arylene, substituted arylene, heteroarylene, or substituted heteroarylene;

S* is a Lewis acid stabilizing group that forms a noncovalent bond with the functional group and thereby maintains the functionalized olefinic monomer in a single stereochemical configuration relative to the ionic or zwitterionic catalyst throughout each of said successive reactions, thereby preventing rearrangement of the functionalized olefin relative to the catalyst during each successive reaction;

$R^2$ is aryl, substituted aryl, heteroaryl, substituted heteroaryl, or —$R^1$—S*;

Q is a hydrocarbylene, substituted hydrocarbylene, heteroatom-containing hydrocarbylene, or substituted heteroatom-containing hydrocarbylene linker, and further wherein two or more substituents on adjacent atoms within Q may be linked to form a cyclic group; and $Q^1$ and $Q^2$ are univalent radicals, and further wherein, in the structure of formula (Ia), either $R^2$ bears a negative charge or the complex is cationic and ionically associated with a negatively charged counterion.

2. The method of claim 1, wherein the olefinic carbon atom is directly substituted with the functional group.

3. The method of claim 1, further comprising simultaneously contacting a second olefinic monomer with the transition metal complex or precursor thereto, so that the polyolefin is a copolymer.

4. The method of claim 3, wherein the second olefinic monomer is not substituted with a functional group.

5. The method of claim 1, wherein:

the functional group is selected from hydroxyl, $C_1$–$C_{20}$ alkoxy, $C_2$–$C_{20}$ alkenyloxy, $C_2$–$C_{20}$ alkynyloxy, $C_5$–$C_{20}$ aryloxy, $C_2$–$C_{20}$ alkylcarbonyl, $C_6$–$C_{20}$ arylcarbonyl, $C_2$–$C_{20}$ alkylcarbonyloxy, $C_6$–$C_{20}$ arylcarbonyloxy, $C_2$–$C_{20}$ alkoxycarbonyl, $C_6$–$C_{20}$ aryloxycarbonyl, carboxy, carboxylato, carbamoyl, mono-($C_1$–$C_{20}$ alkyl)-substituted carbamoyl, di-($C_1$–$C_{20}$ alkyl)-substituted carbamoyl, mono-($C_1$–$C_{20}$ alkyl)-substituted $C_6$–$C_{20}$ arylcarbamoyl, di-($C_1$–$C_{20}$ alkyl)-substituted $C_6$–$C_{20}$ arylcarbamoyl, mono-($C_1$–$C_{20}$ alkyl)-substituted amino, di-($C_1$–$C_{20}$ alkyl)-substituted amino, mono-($C_5$–$C_{20}$ aryl)-substituted amino, di-($C_5$–$C_{20}$ aryl)-substituted amino, $C_2$–$C_{20}$ alkylamido, $C_6$–$C_{20}$ arylamido, imino, alkylimino, or arylimino; and S* is selected from —$OBE_2$, —$OAlE_2$, —$OPE_2$, —$OSnE_3$, —$OSiE_3$, or —OZnE, wherein E is selected from halide, hydroxyl, $C_1$–$C_{12}$ alkyl, $C_1$–$C_{12}$ alkoxy, $C_5$–$C_{14}$ aryl, or $C_5$–$C_{14}$ aryloxy.

6. The method of claim 5, wherein:

the functional group is selected from hydroxyl, $C_1$–$C_{20}$ alkoxy, $C_2$–$C_{20}$ alkenyloxy, $C_2$–$C_{20}$ alkynyloxy, $C_5$–$C_{20}$ aryloxy, $C_2$–$C_{20}$ alkylcarbonyl, $C_6$–$C_{20}$ arylcarbonyl, $C_2$–$C_{20}$ alkylcarbonyloxy, $C_6$–$C_{20}$ arylcarbonyloxy, $C_2$–$C_{20}$ alkoxycarbonyl, or $C_6$–$C_{20}$ aryloxycarbonyl; and the stabilizing group is selected from —$OAlCl_2$, —$OAl(CH_3)_2$, —$OSn(CH_3)_3$, or —OZnO— phenyl.

7. The method of claim 1, wherein w is 2, $M^1$ is Pd(II), Fe(II), Co(II), or Ni(II), x is 1, and y is 1.

8. The method of claim 7, wherein Q has the structure of formula (II)

$$\text{(II)}$$

such that the transition metal complex has the structure of formula (III) and the onic or zwitterionic catalyst has the structure of formula (IIIa)

$$\text{(III)}$$

$$\text{(IIIa)}$$

wherein:

wherein q is an optional double bond;

$R^3$, $R^4$, $R^5$ and $R^6$ are independently selected from hydrogen, hydrocarbyl, substituted hydrocarbyl, heteroatom-containing hydrocarbyl, or substituted heteroatom-containing hydrocarbyl, wherein any substituents present may include Lewis acid stabilizing moieties that may or may not be the same as S* and further wherein any two or more of $R^1$, $R^2$, $R^3$, $R^4$, $R^5$ and $R^6$ may be taken together to form a cyclic group;

z is zero or 1, and further wherein, in the structure of formula (IIIa), either $R^2$ bears a negative charge or the complex is associated with a negatively charged counterion.

9. The method of claim 8, wherein $X^1$ and $X^2$ are N.

10. The method of claim 9, wherein z is zero.

11. The method of claim 10, wherein $R^3$ and $R^4$ are hydrogen or methyl, $M^1$ is Pd(II) or Ni(II), x is 1, y is 1, and $Q^1$ or $Q^2$ are independently selected from Cl, Br, and $CH_3$.

12. The method of claim 11, wherein the complex is of the formula [Ar—N═C($CH_3$)—C($CH_3$)═N—Ar]$PdCl_2$, [Ar—N═C($CH_3$)—C($CH_3$)═N—Ar]Pd($CH_3$)Cl, [Ar—N═C($CH_3$)—C($CH_3$)═N—Ar]Pd($CH_3$)$_2$, or [Ar—N═C($CH_3$)—C($CH_3$)═N—Ar]$NiBr_2$, wherein Ar is 2,4,6-trimethylphenyl substituted at the 3-position with S*.

13. The method of claim 10, wherein $R^1$ is arylene or substituted arylene, $R^2$ and $R^4$ taken together form a pyridine ring, $R^3$ is hydrogen, $M^1$ is Pd(II) or Ni(II), x is 1, y is 1, and $Q^1$ or $Q^2$ are independently selected from Cl, Br, and $CH_3$.

14. The method of claim 13, wherein the complex is of the formula [Ar—N=C(H)-2-pyridine]PdCl$_2$, [Ar—N=C(H)-2-pyridine]Pd(CH$_3$)Cl, [Ar—N=C(H)-2-pyridine]Pd(CH$_3$)$_2$, or [Ar—N=C(H)-2-pyridine]NiBr$_2$, wherein Ar is 2,4,6-trimethylphenyl substituted at the 3-position with S*.

15. The method of claim 1, wherein the activator is a salt or acid of a weakly coordinating anion.

16. The method of claim 15, wherein the weakly coordinating anion is selected from tetrakis[3,5-bis(trifluoromethyl)phenyl]borate, tetrakis(pentafluorophenyl)borate, tetraphenylborate, tetrafluoroborate, trifluoromethanesulfonate, p-toluenesulfonate, SbF$_6^-$, or PF$_6^-$.

17. The method of claim 1, wherein the polyolefin prepared is stereoregular.

18. The method of claim 1, wherein the functionalized olefinic monomer is vinyl acetate.

19. The method of claim 1, wherein the functionalized olefinic monomer is a vinyl ether.

20. The method of claim 19, wherein the vinyl ether is a lower alkyl vinyl ether.

21. The method of claim 4, wherein the functionalized olefinic monomer is vinyl acetate, the second olefinic monomer is ethylene, and the polyolefin is poly(ethylene vinyl acetate).

22. A method for preparing a polyolefin substituted with pendant functional groups, comprising contacting, under polymerization conditions, (a) a functionalized olefinic monomer composed of an olefin directly or indirectly substituted on an olefinic carbon atom with a polar, electron-donating functional group, with (b) a precursor to a transition metal complex, the precursor having the structure,

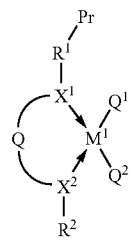

and (c) an activator that converts the precursor to an ionic or zwitterionic catalyst which facilitates stepwise polymer synthesis by successive insertion reactions of olefinic monomers, the ionic or zwitterionic catalyst having the structure of formula (Ia)

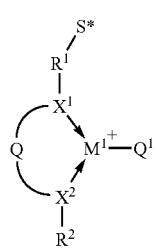

(Ia)

wherein:

M$^1$ is a transition metal selected from Pd(II), Fe(II), Co(II), Ni(II), V(IV), Zr(IV), Hf(IV), Ti(IV), Ru(II), Rh(II), Os(II), Ir(II), or Pt(II);

x and y are integers in the range of zero to w, and the sum of x and y is w;

X$^1$ and X$^2$ are heteroatoms coordinated to M$^1$;

Pr is a moiety that is converted to S* in the presence of the activator, and R$^2$ is optionally substituted with Pr;

R$^1$ is arylene, substituted arylene, heteroarylene, or substituted heteroarylene;

S* is a Lewis acid stabilizing group that forms a noncovalent bond with the functional group and thereby maintains the functionalized olefinic monomer in a single stereochemical configuration relative to the ionic or zwitterionic catalyst throughout each of said successive reactions, thereby preventing rearrangement of the functionalized olefin relative to the catalyst during each successive reaction;

R$^2$ is aryl, substituted aryl, heteroaryl, substituted heteroaryl, or —R$^1$—Pr;

Q is a hydrocarbylene, substituted hydrocarbylene, heteroatom-containing hydrocarbylene, or substituted heteroatom-containing hydrocarbylene linker, and further wherein two or more substituents on adjacent atoms within Q may be linked to form a cyclic group; and Q$^1$ and Q$^2$ are univalent radicals, and further wherein, in the structure of formula (Ia), either R$^2$ bears a negative charge or the complex is cationic and ionically associated with a negatively charged counterion.

23. The method of claim 22, wherein the activator is of the formula ME$_c$Lg in which M is B, Al, P, Sn, Si, or Zn, E is selected from halide, hydroxyl, halide, C$_1$–C$_{12}$ alkyl, C$_1$–C$_{12}$ alkoxy, C$_5$–C$_{14}$ aryl, or C$_5$–C$_{14}$ aryloxy, Lg is a leaving group, and c is 1, 2, or 3.

24. The method of claim 22, wherein R$^2$ is substituted with Pr.

25. The method of claim 24, wherein the activator is of the formula ME$_c$Lg in which M is B or Al and E is chloro, bromo, alkoxy, or lower alkyl, or phenyl.

26. The method of claim 22, wherein R$^2$ is negatively charged, such that the transition metal complex is zwitterionic.

27. The method of claim 22, wherein the transition metal complex is cationic and ionically associated with a negatively charged counterion.

28. The method of claim 22, wherein the precursor has the structure

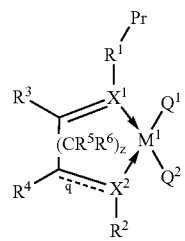

in which Q$^1$, Q$^2$, R$^1$, R$^2$, X$^1$, X$^2$, and M$^1$, are as defined previously, Pr is a moiety that is converted to S* in the presence of the activator, and R$^2$ is optionally substituted with Pr;

R$^3$, R$^4$, R$^5$ and R$^6$ are independently selected from hydrogen, hydrocarbyl, substituted hydrocarbyl, heteroatom-containing hydrocarbyl, or substituted heteroatom-containing hydrocarbyl, wherein any substituents present may include precursors to Lewis acid stabilizing moieties that may or may not be the same as S*, and further wherein any two or more of $R^1$, $R^2$, $R^3$, $R^4$, $R^5$ and $R^6$ may be taken together to form a cyclic group;

q is an optional double bond; and z is zero or 1.

29. The method of claim 28, wherein the activator is of the formula $ME_cLg$ in which M is B, Al, P, Sn, Si, or Zn, E is selected from halide, hydroxyl, halide, $C_1$–$C_{12}$ alkyl, $C_1$–$C_{12}$ alkoxy, $C_5$–$C_{14}$ aryl, or $C_5$–$C_{14}$ aryloxy, Lg is a leaving group, and c is 1, 2, or 3.

30. The method of claim 29, wherein $R^2$ is substituted with Pr.

31. The method of claim 30, wherein the activator is of the formula $ME_cLg$ in which M is B or Al, and E is chloro, bromo, alkoxy, or lower alkyl, or phenyl.

32. The method of claim 28, wherein $R^2$ is negatively charged, such that the transition metal complex is zwitterionic.

33. The method of claim 28, wherein the transition metal complex is cationic and ionically associated with a negatively charged counterion.

34. The method of claim 28, wherein the complex is of the formula [Ar—N═C(CH$_3$)—C(CH$_3$)═N—Ar]PdCl$_2$, [Ar—N═C(CH$_3$)—C(CH$_3$)═N—Ar]Pd(CH$_3$)Cl, [Ar—N═C(CH$_3$)—C(CH$_3$)═N—Ar]Pd(CH$_3$)$_2$, or [Ar—N═C(CH$_3$)—C(CH$_3$)═N—Ar]NiBr$_2$, wherein Ar is 2,4,6-trimethylphenyl substituted at the 3-position with a hydroxyl group.

35. The method of claim 28, wherein $R^1$ is arylene or substituted arylene, $R^2$ and $R^4$ taken together form a pyridine ring, $R^3$ is hydrogen, $M^1$ is Pd(II) or Ni(II), x is 1, y is 1, and $Q^1$ and $Q^2$ are independently selected from Cl, Br, or CH$_3$.

* * * * *

Adverse Decision in Interference

Patent No. 7,037,990, Christopher D. Tagge, Robert B. Wilson, Jr. and Hiroyuki Ono, TRANSITION METAL COMPLEXES IN THE CONTROLLED SYNTHESIS OF POLYOLEFINS SUBSTITUTED WITH FUNCTIONAL GROUPS, Interference No. 105,584, final judgment adverse to the patentees rendered December 5, 2007 as to claims 1-35.

*(Official Gazette August 5, 2008)*